(12) United States Patent
    Ralston et al.

(10) Patent No.: US 7,602,501 B2
(45) Date of Patent: Oct. 13, 2009

(54) INTERFEROMETRIC SYNTHETIC APERTURE MICROSCOPY

(75) Inventors: Tyler S. Ralston, Waltham, MA (US); Daniel L. Marks, Urbana, IL (US); Paul Scott Carney, Champaign, IL (US); Stephen A. Boppart, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 120 days.

(21) Appl. No.: 11/775,572

(22) Filed: Jul. 10, 2007

(65) Prior Publication Data

US 2008/0140341 A1   Jun. 12, 2008

Related U.S. Application Data

(60) Provisional application No. 60/819,593, filed on Jul. 10, 2006.

(51) Int. Cl.
    *G01B 11/02* (2006.01)
(52) U.S. Cl. .................................... 356/497
(58) Field of Classification Search ............. 356/479, 356/497
    See application file for complete search history.

(56) References Cited

U.S. PATENT DOCUMENTS

| 5,956,355 | A | * | 9/1999 | Swanson et al. ............. 372/20 |
| 5,994,690 | A | * | 11/1999 | Kulkarni et al. ............. 250/216 |
| 2004/0127782 | A1 | * | 7/2004 | Sfez et al. .................... 600/407 |

OTHER PUBLICATIONS

Ralston et al., "*Deconvolution Methods for Mitigation of Transverse Blurring in Optical Coherence Tomography*", IEEE Transactions on Image Processing, vol. 14, No. 9, pp. 1254-1264, Sep. 2005.

Ralston et al., "*Demonstration of inverse scattering in optical coherence tomography*", Proceeding of the SPIE, vol. 6079, pp. 60791T-1-60791T-9, Feb. 20, 2006.

Bruno & Chaubell, "*One-dimensional inverse scattering problem for optical coherence tomography*", Institute of Physics Publishing, Inverse Problems, vol. 21, pp. 499-524, Feb. 23, 2005.

Choma et al., "*Sensitivity advantage of swept source and Fourier domain optical coherence tomography*", Optics Express, vol. 11, No. 18, pp. 2183-2189, Sep. 8, 2003.

International Searching Authority, Patent Cooperation Treaty International Search Report, PCT/US2007/073146, dated Mar. 18, 2008, 12 pages.

Carney, "ECE 569: Lecture 15", Department of Electrical and Computer Engineering, University of Illinois at Urbana—Champaign, Urbana, IL, 2004.

(Continued)

*Primary Examiner*—Tarifur Chowdhury
*Assistant Examiner*—Jonathon D. Cook
(74) *Attorney, Agent, or Firm*—Sunstein Kann Murphy & Timbers LLP

(57) ABSTRACT

Methods and apparatus for three-dimensional imaging of a sample. A source is provided of a beam of substantially collimated light characterized by a temporally dependent spectrum. The beam is focused in a plane characterized by a fixed displacement along the propagation axis of the beam, and scattered light from the sample is superposed with a reference beam derived from the substantially collimated source onto a focal plane detector array to provide an interference signal. A forward scattering model is derived relating measured data to structure of an object to allow solution of an inverse scattering problem based upon the interference signal so that a three-dimensional structure of the sample may be inferred in near real time.

16 Claims, 18 Drawing Sheets

OTHER PUBLICATIONS

Davis et al., "Autocorrelation artifacts in optical coherence tomography and interferometric synthetic aperture microscopy", Optic Letters, pp. 1441-1443, vol. 32, No. 11, Jun. 1, 2007.

Yasuno, et al., "Non-iterative numerical method for laterally super-resolving Fourier domain optical coherence tomography", Optics Express, pp. 1006-1020, vol. 14, No. 3, Jan. 2006.

Davis et al., "Nonparaxial vector-field modeling of optical coherence tomography and interferometric synthetic aperture microscopy", J. Opt. Soc. Am. A, vol. 24, No. 9, Sep. 2007.

Ralston et al., "Inverse scattering for optical coherence tomography", J. Opt. Soc. Am. A, vol. 23, No. 5, May 2006.

* cited by examiner

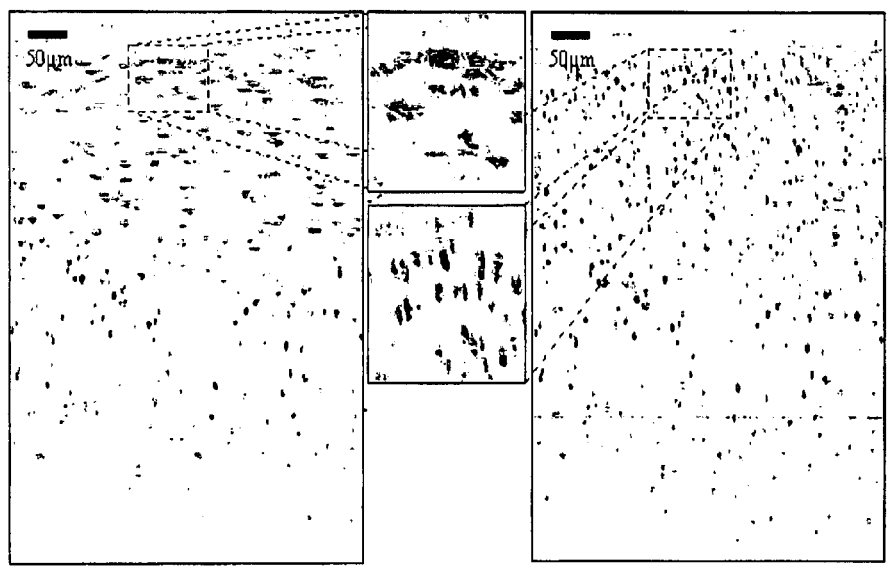
*FIG. 2(a)*          *FIG. 2(b)*

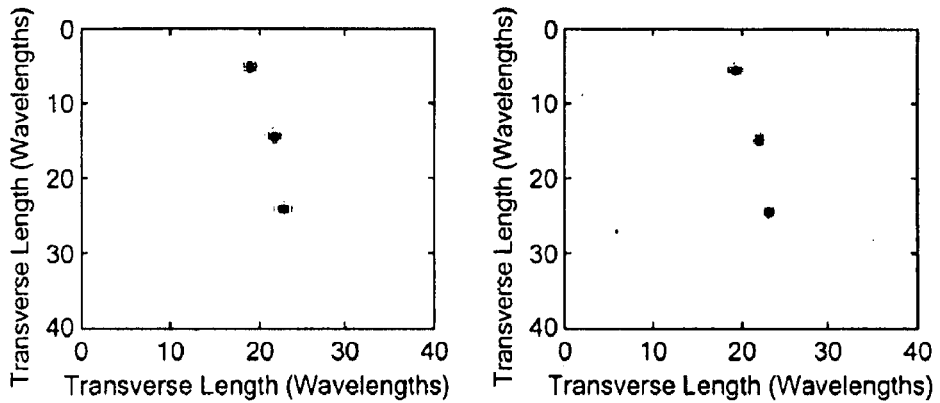
FIG. 4(a) PLANE A
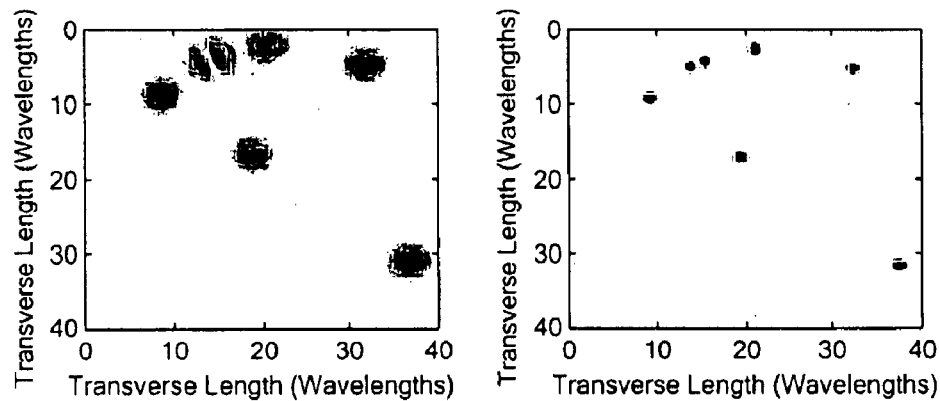
FIG. 4(b) PLANE B
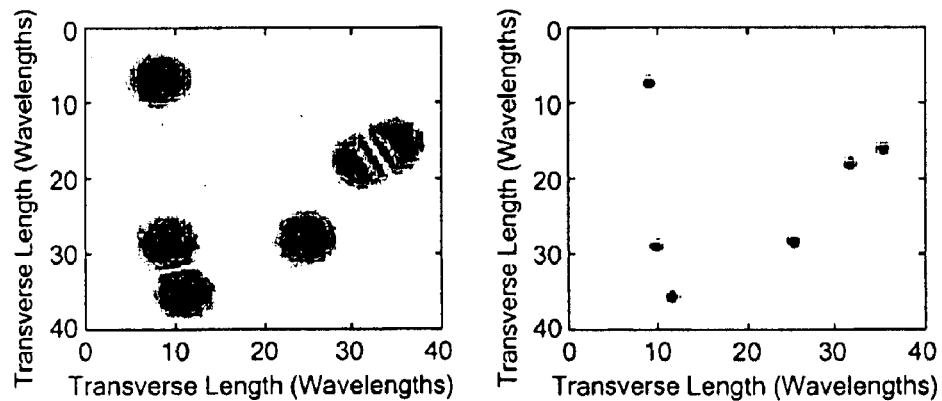
FIG. 4(c) PLANE C

INTERFEROMETRIC SYNTHETIC APERTURE MICROSCOPY

The present application claims the priority of U.S. Provisional Patent Application Ser. No. 60/819,593, filed Jul. 10, 2006, which is incorporated herein by reference.

The present invention has been developed, in part, with Government support under Contract Numbers 02390265 and BES 05-19920, awarded by the National Science Foundation, and Contract Number 1 R21 EB005321, awarded by the National Institutes of Health. The Government has certain rights in the invention.

TECHNICAL FIELD

The present invention pertains to a computed imaging method for three-dimensional interferometric determination of the susceptibility of an object on the basis of coherently detected backscattered radiation, and, more particularly, to a method for providing improved resolution outside of the limited volume (the confocal volume) that can be resolved in focus for typical optical, acoustic, and other microscopes.

BACKGROUND OF THE INVENTION

Optical coherence tomography (OCT), as employed for imaging through scattering media, with significant applications for medical imaging, is typically based upon the notion of coherently ranging scatterers in a focal volume using a high-bandwidth, low temporal coherence source, such as a superluminescent diode. By measuring the interferometric cross-correlation between a reference beam and the backscattered return beam, the scatterers corresponding to a particular time delay, typically corresponding to a depth in the medium, can be ranged. Techniques employing OCT are surveyed in Bouma et al., *Handbook of Optical Coherence Tomography* (Marcel Dekker, 2001), which is incorporated herein by reference. Optical coherence microscopy (OCM), described, for example, by Schmitt et al., *Subsurface Imaging of Living Skin with Optical Coherence Microscopy, Dermatology*, vol. 191, pp. 93-98 (1995) and Izatt, *Optical Coherence Microscopy in Scattering Media, Optics Letters*, vol. 19, pp. 590-592 (1994), incorporated by reference herein, combines the depth-ranging capability of OCT with confocal microscopy to obtain micron-scale imaging beneath the surface of a scattering medium.

Traditional OCT operates by illuminating the object with a focused, broadband beam. The back-scattered light is collected, and by using interferometric detection, the time delay and therefore the distance along the beam to scatterers inside the object is determined. By scanning the beam through the object, the locations of scatterers in three dimensions can be found. The resolution of OCT in the axial direction, along the direction of propagation of the beam, is determined primarily by the bandwidth of the light source. However, the resolution in the transverse direction is not constant along the beam. At the focus of the beam, the resolution is determined by the focused spot size, but away from the focus, the resolution degrades because the beam is diverging or converging. This loss of resolution is usually assumed to be an inevitable consequence of defocus. Because the depth-of-field or the confocal volume decreases in size as the numerical aperture of the illumination and detection optics increase, improved transverse resolution results, according to current practice, in a smaller range of depths that can be resolved for a typical OCT system unless the focus is mechanically scanned. "Confocal volume," as used herein, refers to a volume that is essentially in focus, within a specified criterion, at a single relative placement of the sample relative to the optical system.

SUMMARY OF THE INVENTION

In accordance with preferred embodiments of the present invention, a method is provided for determining the three-dimensional susceptibility of a sample. The method has steps of:

a. providing a source of a beam of radiation characterized by a temporally dependent spectrum and a local propagation axis;

b. irradiating the surface in a plane characterized by a fixed displacement along the propagation axis of the beam;

c. superposing scattered radiation from the sample with a reference beam derived from the source of the beam to provide an interference signal;

d. deriving a forward scattering model relating measured data to structure of an object; and e. solving an inverse scattering problem based upon the interference signal to infer a three-dimensional susceptibility of the sample.

In accordance with alternate embodiments of the invention, the forward scattering model may relate a transform of measured data to a transform of structure of the sample. A step may additionally be provided of transforming the interference signal into a transform of the interference signal in a transform domain. The step of solving an inverse scattering problem may be performed in substantially real time.

In accordance with further embodiments of the invention, the step of irradiating may include focusing radiation substantially at the surface of the sample, such as through a microscope objective. It may also include delivering the beam to the irradiated sample by at least one of a catheter, a needle, a probe, an endoscope, or a laparoscope. The method may also entail sweeping the spectrum of the source of radiation as a function of time.

In other embodiments of the invention, a tunable laser may be provided as the source of radiation. The step of superposing scattered radiation from the sample with a reference beam may include configuring arms of the beam in an interferometer, such as a Michelson a Mach-Zehnder, and a Fizeau interferometer.

In accordance with another aspect of the invention, an interferometric synthetic aperture microscope (ISAM) is provided that has a source of substantially coherent illumination for illuminating an object subject at a fixed focal distance relative to a fiducial position defined with respect to the microscope. The ISAM also has a reference arm for relaying a portion of the coherent illumination onto a focal plane sensor, a telescope for relaying a field scattered by an object onto the focal plane sensor, and a processor for deconvolving the field measured by the focal plane sensor to recover a three-dimensional image of the object. The reference arm, in particular, may be a fixed reference mirror.

BRIEF DESCRIPTION OF THE DRAWINGS

The foregoing features of the invention will be more readily understood by reference to the following detailed description, taken with reference to the accompanying drawings, in which:

FIG. 2(a) is an example of OCT data derived from microparticles embedded in a tissue phantom outside of the focus, while FIG. 2(b) is an ISAM reconstruction of the data.

FIG. 3(c) shows the projection of the simulated data collapsed (summed) along one transverse direction, while

FIGS. 4(a)-4(c) show three pairs of en face images of the time-domain data (left side) and the reconstructed volume (right).

DETAILED DESCRIPTION OF SPECIFIC EMBODIMENTS

The following detailed description may be more fully understood by reference to Ralston et al., *Inverse Scattering for Optical Coherence Tomography*, J. Opt. Soc. Am. A, vol. 23, pp. 1027-37 (May, 2006), which is appended hereto, and incorporated herein by reference.

Figure 1:
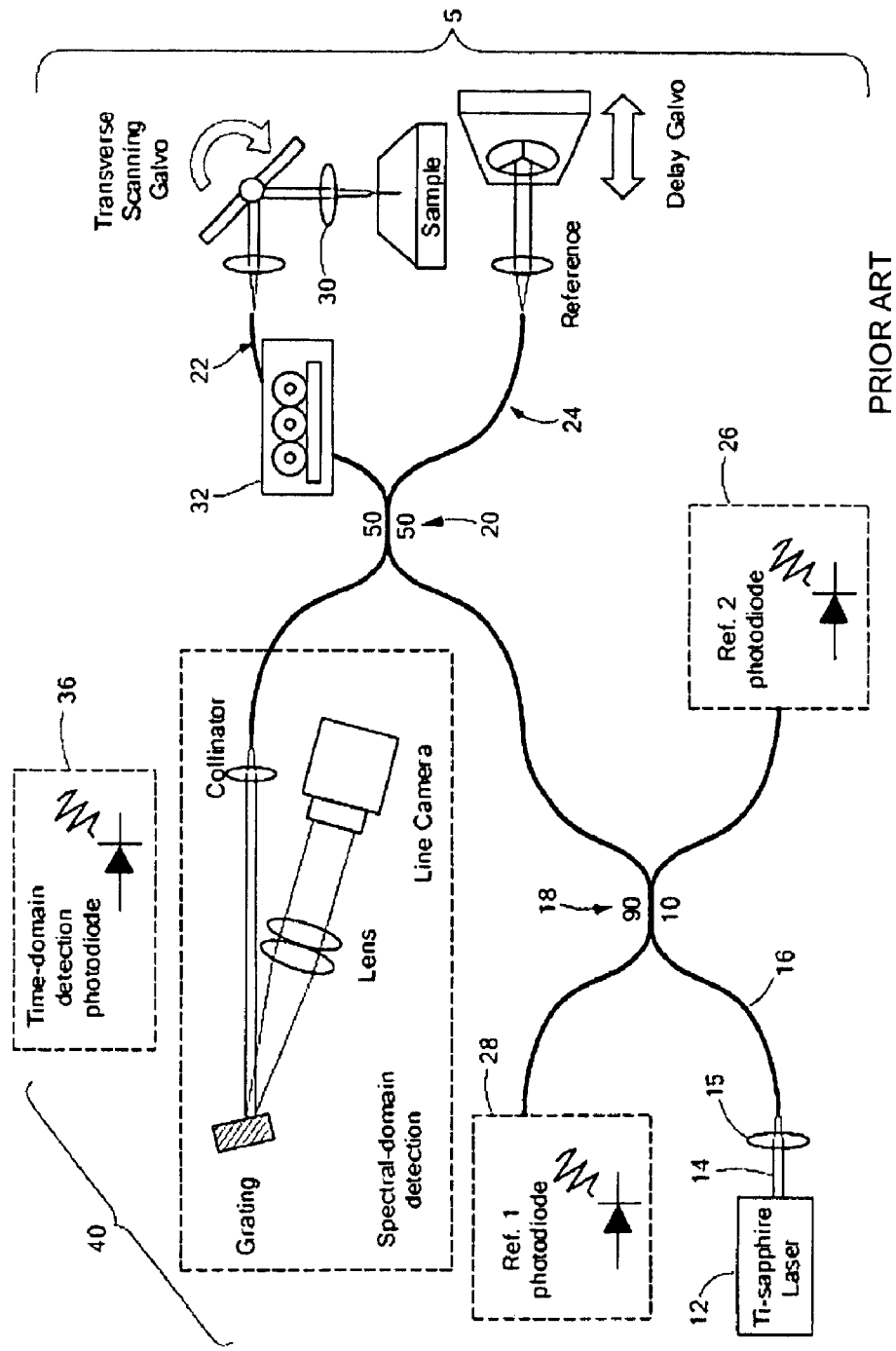
FIG. 1 is an exemplary schematic depiction of an optical coherence tomography system in its time-domain and spectral-domain variants.

FIG. 1 shows an example of an OCT system, designated generally by numeral 5, including options to detect the cross-correlation signal in either the spectral domain or the time domain. This particular OCT system uses a coherent light source 12, such as a neodymium:vanadate (Nd:YVO$_4$) pumped titanium:sapphire laser. In the exemplary embodiment depicted, a center wavelength of 800 nm and an average bandwidth of 100 nm yields an axial resolution of ~2 µm in tissue. The beam 14 is launched, via coupling optics 15, into a fiber-optic cable 16 and connected to a pair of fiber-optic beam splitters 18, 20 (Gould Fiber Optics, Inc., Millersville, Md.). The interferometer employs a single-mode 50/50 fiber optic splitter 20 that delivers and couples the signals to and from the sample arm 22 and the galvanometer-based reference arm 24. The 90/10 beam splitter 18 serves the purpose of producing a reference spectrum for source noise reduction in the balanced photodetector. This setup can make use of both the single photodetector and the high-speed dual balanced photodetectors 26 and 28. In the sample arm, interchangeable achromatic lenses 30, from 9 mm to 40 mm, can be used to focus from 10 mW to 30 mW of light down to corresponding spot size (determined by transverse resolution). Polarization paddles 32 in the sample arm are able to change the polarization incident upon the sample to achieve maximum interference.

A time-domain system is characterized by capturing axial scans while a reference arm 24 varies the path length in relation to the sample arm 22. There are several designs of varying the path length in the reference arm. In certain embodiments, reference arms may include a standard spatial domain delay, or a rapid scanning optical delay (RSOD) which employs a spatial Fourier shift to create a delay. Typically, a single or dual-balanced photodetector 36 is used to capture interference data.

A spectral-domain system is characterized by capturing the spectrum of a light source and inferring the spatial axial susceptibility. Susceptibility describes, in theoretical terms, the dielectric properties of a material that give rise to scattering and thus to the representation ordinarily considered to constitute an image. There are several ways to detect the spectrum including employing a frequency swept laser and detection with a single photodetector, or a broadband laser and detection using an imaging grating spectrometer 40 so that all frequencies are detected simultaneously.

In order to elucidate the present invention, a theory of inverse scattering is presented that has been developed for optical coherence tomography (OCT) and that is used to resolve three-dimensional object structure, taking into account the finite beam width and focusing. While the invention is described herein in optical terms, it is to be understood that the invention is not so limited, and that the teachings provided herein are equally applicable to any radiation, whether acoustic or of other particles, massive or otherwise, that may be characterized in terms of wave propagation.

By using the invention, transverse and axial resolution produced by conventional OCT imaging inside the confocal volume can be achieved outside of the confocal volume. Explicitly, experiments show that scatterers can be resolved outside of the confocal volume with resolution comparable to that achievable inside the confocal volume. Numerical simulations and experimental results demonstrate the effectiveness of this technique. When the algorithm is applied to experimentally-acquired OCT data, the transverse and axial resolutions outside of the confocal parameter are improved, extending the apparent confocal parameter range. These results further improve the high-resolution cross-sectional imaging capabilities of OCT.

To illustrate the problem in OCT that is solved with ISAM, a sample is designed and imaged, which clearly shows the effect of the probing beam. A tissue phantom, a collection of titanium dioxide scatterers having a mean diameter of 1 μm suspended in silicone, was imaged with a spectral-domain OCT (SD-OCT) system. FIG. 2(a) displays the OCT data with no beam consideration. The 2D ISAM reconstructed image of an area of 500 pm (transverse) by 1000 μm (axial) is depicted in FIG. 2(b), where the bandwidth is 100 nm, the focal length of the lens is 15 mm, the spot size is 11 μm, and the confocal parameter is 996 μm. The image resolution of point scatterers outside of the confocal region for the original experimental image data is not constant, but for the reconstruction, the resolution is relatively constant along the entire image with only amplitude variations. The interference between the light scattered from a group of adjacent particles (boxed) is evident in the original image (top magnified). Methods in accordance with the present invention properly rephase the signal from scatterers to produce a well-resolved image (bottom magnified).

The sample imaged in FIG. 2 consists of a uniform number of scatterers, yet when looking at the reconstruction the number of scatters outside of the confocal region seems to increase. The 2D equivalent of the algorithm resolves only a perpendicular projection of the 3D data set. The imaging beam has a wider contour outside of the confocal region, and thus the beam is incident upon a larger volume illuminating more scatterers.

ISAM fundamentally relies on the solution of the inverse scattering problem, $S=K\eta$, where K is a linear operator which transforms the collected signal S to the object's spatial susceptibility $\eta$. (The dimensionalities of S and $\eta$ are discussed below.) In some geometries, K can be diagonalized in the Fourier domain producing an efficient algorithm for attaining spatially invariant resolution.

There are many embodiments for ISAM, each of which relies on specific imaging geometries and the various embodiments may advantageously be employed in variations on the instrumentation. Different geometries require somewhat different formulations of the forward and inverse scattering problems. Included here are the solutions for three geometries that are most likely to be useful in practice. The first geometry, for a Gaussian beam with a focus transversely scanned over a plane, is the most often used geometry of OCT when external surfaces are to be imaged. The second geometry, for an azimuthally scanned beam, is typically employed for catheters for imaging internally inside the human body, and may be utilized in applications wherein the beam is delivered to the irradiated sample by a needle, a probe, an endoscope, or a laparoscope. Finally, the full-field geometry is useful when external surfaces are to be imaged and speed of data acquisition is paramount. Other instruments will likely be amenable to be adapted to these geometries, and the ability to perform ISAM is not limited to these geometries. The types of incident fields that we have specifically addressed are focused Gaussian beams and plane waves because they are the most common and readily produced and detected beams used for OCT, however the scope of the present invention is not limited to these types of incident field.

In accordance with embodiments of the present invention, the capabilities of both OCT and OCM are greatly extended by computed imaging and synthetic aperture techniques. Among recently demonstrated advantages is the ability to resolve features in the sample that are outside of the confocal region. A more quantitatively accurate and faithful representation of the sample structure than hitherto available is provided by solution of the inverse scattering problem as applied both to full-field planar OCT/OCM as well as to OCT from an azimuthally-scanned catheter. In either case, and in accordance with preferred embodiments of the invention, the focus may advantageously remain fixed at the surface of the sample, while computed imaging techniques are used to infer the structure inside and outside of the depth-of-field. By applying the invention, the focus need not be scanned through the sample.

As further described below, a forward scattering model is derived which relates the measured data to the object structure. From this model, a solution of the inverse scattering problem is obtained that infers the object structure from the data. The achievable resolution and system bandpass is also derived from this forward model, and application of the method is demonstrated by means of a simulation.

Full-Field Non-Scanned Beam Implementation

By means of the novel methods described herein, computed imaging techniques are employed to reconstruct features that are both inside and outside the focus. Instead of scanning the focus through the sample, the focus is fixed at the surface of the sample, and no relative translation is needed between the objective and the sample. A frequency-swept source can be utilized to provide a new degree of freedom, replacing information lost by fixing the focus, without sacrificing detail outside of the focus. Because the objective and sample can remain fixed relative to each other, no translation hardware is needed which makes placing the objective on a fiber optic or a handheld probe easier. This method may lead to faster and more accurate full-field OCT imaging because data acquisition can be very rapid, requiring only that the two-dimensional interferogram is sampled while the frequency of the source is scanned. By virtue of computational image formation, the need to physically form an image of each plane in the volume, as typically done in full-field OCT, is obviated. As data acquisition speed and computational speed continue to increase, video-rate scanning of three-dimensional volumes may become possible.

In order to provide an understanding of computational image formation in the context of full-field OCT, a physical model for the scattering process is developed, and from this, a relationship between the data and the object structure is derived. Based on this relationship, the inverse scattering problem is solved to infer the sample structure from the data.

Full-field OCT allows an entire plane of scatterers to be ranged simultaneously, which makes it a very rapid way to acquire the structure of a volume. A full-field OCT system that is typical of the current state-of-the-art consists of a Michelson interferometer, again, with a broadband illumination source. Reference and sample beams are derived from the broadband source using a beam splitter. An extended area of the sample is illuminated by a broadband collimated beam through a microscope objective. The objective is focused at the depth of features of interest. A signal is scattered by the sample back through the objective. A reference beam is delayed to return to the beam splitter at the same time the signal scattered from the focus arrives. The reference and signal are superimposed and focused on a focal plane array (such as a charge-coupled device (CCD) sensor) which detects the interference signal. The amplitude of the interference signal corresponds to the reflections of scatterers at the focus plane. By translating the sample through the focus plane, the scatterers at many different depths may be ranged.

While this method can be used to obtain high resolution images for entire volumes of a sample quickly, it has a number of disadvantages. First, the sample and microscope objective must be translated relative to each other, which is relatively slow and requires fine positioning. Second, this method uses time-domain detection that produces a lower signal-to-noise ratio than Fourier-domain, or frequency-swept, OCT.

Figure 3A:
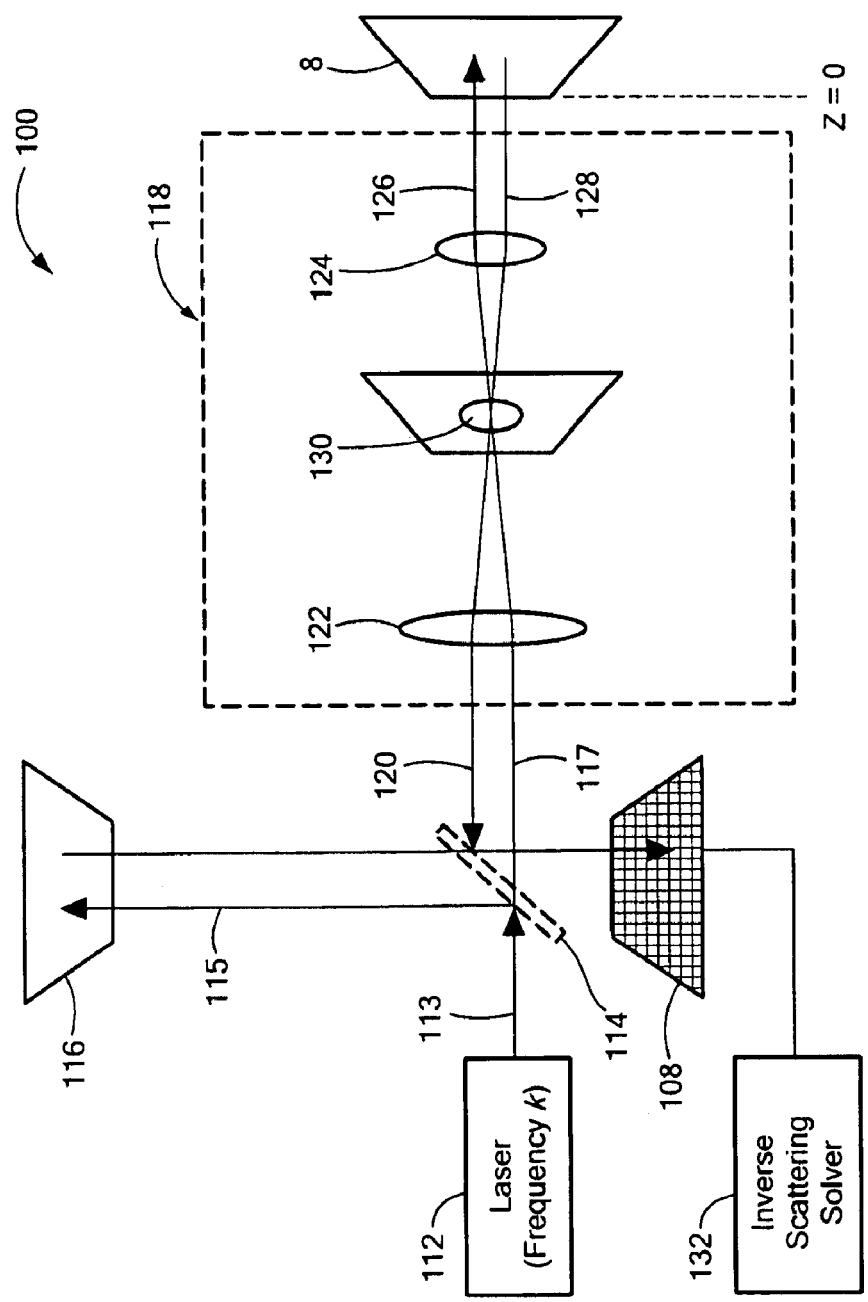
FIG. 3(a) is a schematic depiction of a full-field OCT system in accordance with a preferred embodiment of the present invention.

A full-field OCT system, in accordance with embodiments of the present invention, is now described with reference to FIG. 3(a) and is designated generally by numeral 100. While system 100, as shown, is based on a Michelson interferometer, other interferometric configurations such as that of a self-referencing Fizeau design, may be used and are encompassed within the scope of the present invention and of any claims appended hereto. In system 100, the illumination source is a tunable narrow band laser 112. It is to be understood that partially coherent sources may also be employed within the scope of the present invention, where their application is consistent with the methods described, and that references herein to a laser may also encompass sources that lack temporal or spatial coherence, or both, unless the particular context dictates otherwise.

Laser 112 is tuned to wavelengths λ that correspond to spatial frequencies k. Laser 112 nominally emits a plane wave (or is spatially filtered to produce one). The coherence length of this laser should be at least as twice as long as the total depth of the sample 8 under study, to ensure that fields scattered throughout the entire sample simultaneously interfere with the reference field.

Laser illumination 113 is split by a beam splitter 114 into two components. One component 115 travels to a reference mirror (or delay mirror) 116, and is reflected back through the beamsplitter 114 to the output port where the focal plane array 108 is located. It is to be understood that, most generally, numeral 108 designates a detector, and that references to detector 108 as a focal plane array are by way of non-limiting example. The other beam component 117 is demagnified by a factor 1/M using a telescope 118 of magnification M. The purpose of telescope 118 is to concentrate the illumination onto the sample 8, and then relay a magnified scattered field 120 to the focal plane array 108. This telescope consists of two converging lenses: a relay lens 122 and a microscope objective 124. The illumination on the sample is a normally incident plane wave 126. The sample scatters some radiation 128 backwards through the telescope 118. The telescope is aligned to afocally and telecentrically image the front surface of the sample to the focal plane array. Sitter et al., *Three-dimensional Imaging: a Space-invariant Model for Space Variant Systems*, Appl. Opt., vol. 29, pp. 3789-94 (1990) discusses three-dimensional imaging problems, and is incorporated herein by reference.

It is to be noted, significantly, that in a manner distinct from that of standard full-field OCT microscopy, the focus of the objective 124 may remain fixed, in accordance with the present invention, at the surface of sample 8. For purposes of the following heuristic analysis, it is assumed that telescope 118 is aberration free and vignetting inside the telescope is negligible. If the telescope is assumed to correct spherical aberration, then there is a finite volume within the sample space for which these assumptions hold. A pupil 130 is placed at the focus of the illumination beam inside the telescope to spatially filter the backscattered signal so as to enforce a well-defined spatial bandlimit. The response of the telescope is modeled by a space-invariant convolution with a bandwidth determined by the pupil size. At the focal plane array 108, the reference and sample signals superimpose and interfere, and the intensity of the interference is detected. The intereference signal from detector 108 is coupled to an Inverse Scattering Solver 132, the operation of which is now described.

Figure 14:
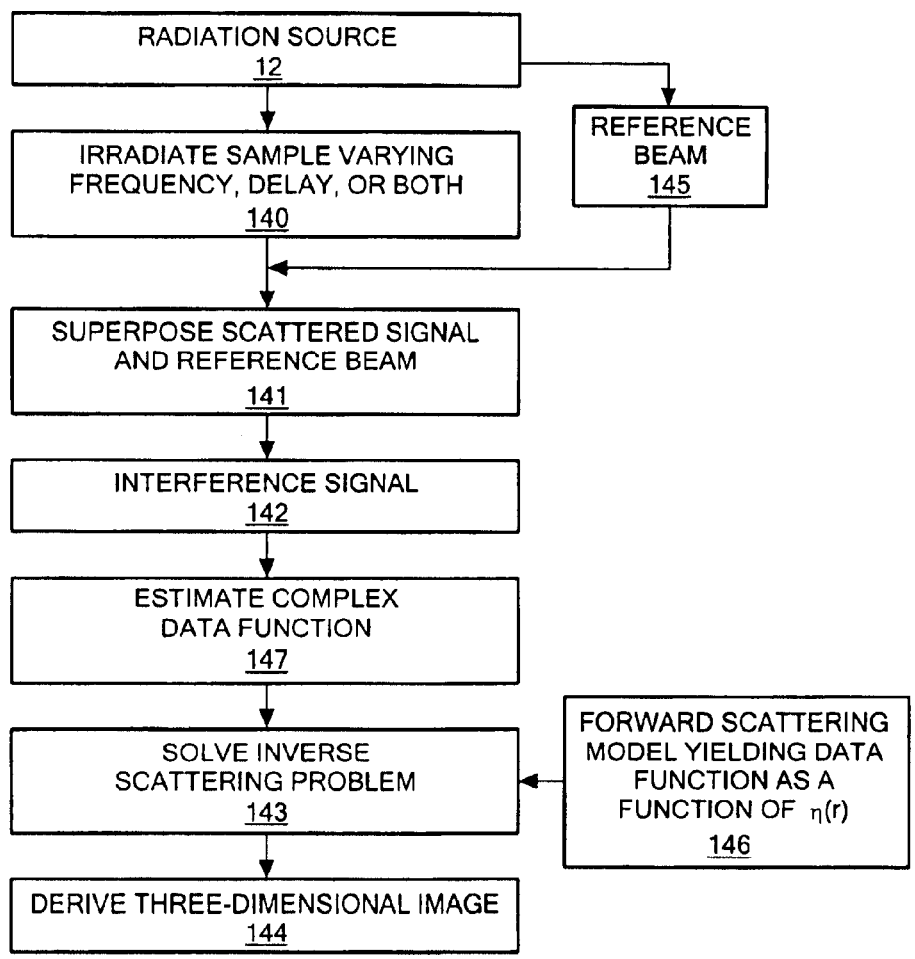
FIG. 14 is a flowchart depicting steps in imaging a sample using in accordance with embodiments of the present invention.

To derive the relationship between the object structure and the data detected on the sensor, a mathematical model of scattering of the illumination field by the object and interferometric detection at the sensor is now described with reference to FIG. 14. For convenience of description, a scalar field is substituted for the electromagnetic field, neglecting polarization effects. The incident field on the sample, provided in step 140, is given by the expression:

$$E_i(r;k) = A(k) \exp(ikz) \tag{1}$$

where r is a location within the volume of sample 8, k is the spatial frequency of the illumination, A(k) is the amplitude of the illumination at frequency k, and $\hat{z}$ is the direction of increasing depth into the sample. For present purposes, it is assumed that the scattering is well-modeled by the weak or first Born scattering approximation, where the scattering by the object is modeled as a source. The susceptibility of the object is given by η(r) such that η(r)=0 for z<0.

The secondary scattered field $E_s(r'; k)$ from the object at the plane z=0 is given by the expression $$E_s(r'; k) = \int_V d^3 r E_i(r; k) \eta(r) \frac{\exp(ik|r'-r|)}{|r'-r|}. \tag{2}$$

To simplify this relationship, it is useful to define the two-dimensional Fourier transform $$\tilde{E}_s(q; k) = \int_{z'=0} d^2 r' E_s(r'; k) \exp(iq \cdot r')$$

with q being a transverse spatial frequency such that $q \cdot \hat{z} = 0$. In terms of q, Eq. (2) is found to be $$\tilde{E}_s(q; k) = A(k) \int_V d^3 r \eta(r) \exp\{i[q \cdot r] + iz[k + k_z(q)]\} k_z(q)^{-1} \tag{3}$$

where $k_z(q) = \sqrt{k^2 - q^2}$, and substituting Eq. (1) into Eq. (2). (In accordance with convention, $x^2$ designates the square modulus of a vector x.) The three-dimensional Fourier transform is defined such that $$\tilde{\eta}(Q) = \int_V d^3r \eta(r)\exp(iQ\cdot r).$$

It is then found that the right-hand integral can be expressed in terms of $\tilde{\eta}(Q)$:

$$\tilde{E}_s(q;k) = A(k)k_z(q)^{-1}\tilde{\eta}\{q+\hat{z}[k+k_z(q)]\} \quad (4)$$

The field $E_f(r;k)$ is produced by the propagation of $E_s(r';k)$ through telescope 118 to focal plane array 108 (shown in FIG. 3(*a*)). Because the telescope is assumed to be an aberration-free telescope which afocally and telecentrically images the plane at the sample z=0 to the focal plane array in the plane z=$z_f$, its function can be modeled by a simple convolution with a point spread function accounting for the finite bandwidth of the telescope, and a magnification factor given by M. The field at the focal plane array is given by $E_f(r;k)$, and the point spread function of the telescope is given by P(r;k). The relationship between $E_f(r;k)$ and $E_s(r';k)$ is $$E_f(r;k) = M^{-1}\int d^2r' E_s(r';k)P(r/M-r';k) \quad (5)$$

where the factor $M^{-1}$ accounts for energy conservation between the two planes.

$$\tilde{E}_f(q;k) = \int_{z=z_f} d^2r E_f(r;k)\exp(iq\cdot r)$$

and the coherent transfer function of the telescope $\tilde{P}(q;k)=\int d^2r\, P(r;k)\exp(iq\cdot r)$, the convolution of Eq. (5) may be expressed as $$\tilde{E}_f(q;k) = M\tilde{E}_s(Mq;k)\tilde{P}(Mq;k) = MA(k)\tilde{P}(Mq;k)k_z(Mq)^{-1}$$
$$\tilde{\eta}\{Mq+\hat{z}[k+k_z(Mq)]\} \quad (6)$$

Eq. (6) specifies a relationship between Fourier components of the field on the focal plane array and those of the object susceptibility.

In accordance with preferred embodiments of the invention, reference mirror 116 is placed to effect a delay on the reference beam 145 of $\tau$ relative to the total delay required for the beam to travel from the beamsplitter 114 to the plane z=0 in the sample arm and back. The reference field $E_r(r; k, \tau)$, relayed to the focal plane array is then given by $$E_r(r;k,\tau) = A(k)\exp[i\omega(k)\tau], \quad (7)$$

where $\omega(k)$ is a dispersion relation relating the temporal frequency with the spatial frequency in the sample medium.

For example, if the object medium is free space, then $\omega(k)=kc$, where c is the speed of light in vacuum. The interference intensity $I(r;k,\tau)=|E_r(r;k,\tau)+E_f(r;k)|^2$ on the focal plane array is then given by $$I(r;k,\tau) = |A(k)|^2+|E_f(r;k)|^2+2A(k)Re\{E_f(r;k)\exp[-i\omega(k)\tau]\}. \quad (8)$$

The part of the signal 142 that is due to interference between the signal and reference beams occurring in step 141 is defined as the data function $D(r;k)=A(k)E_f(r;k)$. The complex $D(r;k)$ can be estimated from measurements of $I(r;k,\tau)$. For example, three measurements of $I(r;k,\tau)$ such that $\omega\tau=0$, $\pi/2$, and $\pi$ may be summed (in step 147 of FIG. 14) to yield, as an approximation:

$$D(r;k) = \frac{1-i}{4}I(r;k,0) - \frac{1+i}{4}I(r;k,\pi/\omega) + \frac{i}{2}I(r;k,\pi/2\omega). \quad (9)$$

The foregoing method of phase-shifting for interferometry is described, for example, in Hariharan, *Optical Interferometry* (Academic Press, 2003), which is incorporated herein by reference. Inserting the results of Eq. (6), the Fourier transform of the data function, which is $\tilde{D}(q;k)=\int d^2r\, D(r;k)\exp(iq\cdot r)$, can be expressed as $$\tilde{D}(q;k) = \tilde{K}(q;k)\tilde{\eta}\{Mq+\hat{z}[k+k_z(Mq)]\}, \quad (10)$$

where, for convenience, the bandpass function is defined $$\tilde{K}(q;k) = MA(k)^2\tilde{P}(Mq;k)k_z(Mq)^{-1} \quad (11)$$

Thus, the data are expressed in terms of the 3-D Fourier transform of the sample structure, and, so, the resolution of the reconstruction of the sample structure is space invariant. However, vignetting and aberrations in the telescope limit the volume over which this resolution can be obtained.

To obtain the measurements needed to reconstruct $\eta(r)$, one must vary both k and $\tau$. In practice, however, it is often slow and inconvenient to adjust both. If one is willing to tolerate some image artifacts, just one of these parameters need be scanned. For simplicity, it is assumed that the pupil function P(r';k) is real and symmetric, which is often the case (for example, when pupil 130 is circular), so that $\tilde{P}(q;k)$ is likewise real and symmetric.

If mirror 116 is fixed such that $\tau=0$, then the imaginary component of D(r;k) is not obtainable. If the imaginary part of D(r;k) is assumed to be zero, then due to the Hermitian symmetry of the Fourier transform of real functions $\tilde{D}(-q,k)=\tilde{D}(q,k)^*$. The function $\tilde{\eta}(Q)$ then also has Hermitian symmetry reflected over the axis. The effect is that a conjugate image of the susceptibility is present, reflected across the plane z=0. Because the delay $\tau=0$ corresponds to the plane z=0, as long as the entire sample is contained such that z>0, the conjugate image and the real image do not overlap. In addition, there is an artifact corresponding to the term $|E_f(r;k)|^2$ in Eq. (8). If the magnitude of the sample signal is small relative to the reference signal, the magnitude of this artifact is also small compared to the real image and can be neglected. This term may also be eliminated by modulating the phase of the reference field and locking in only on the modulation, i.e., by phase-sensitive detection of the intereference signal.

If the delay $\tau$ is scanned, and the laser emits all frequencies k simultaneously (such as occurs in a mode locked laser or a spontaneous emission source), the signal $I_T(r;\tau)$ is the sum of the interference patterns over all emitted frequencies:

$$I_T(r;\tau) = \frac{1}{2\pi}\left[\int_{-\infty}^{\infty}dk\left(\frac{d\omega}{dk}\right)(|A(k)|^2+|E_f(r;k)|^2)\right] + \frac{1}{\pi}Re\left\{\int_{-\infty}^{\infty}dk\left(\frac{d\omega}{dk}\right)D(r;k)\exp[-i\omega(k)\tau]\right\}. \quad (12)$$

The term in square brackets in Eq. (12) is a background intensity that is independent of $\tau$ and therefore is easily subtracted to remove its contribution from the measured intensity. Neglecting the background intensity and the slowly-varying Jacobian $$\left(\frac{d\omega}{dk}\right),$$

Eq. (12) relates the real part of the inverse Fourier transform of D(r;k) with respect to k to the total intensity $I_T(r;\tau)$. To be able to remove the Re{ } operation so that a unique solution for D(r;k) can be found, one equates D(r;-k)=D(r;k)*. Eq. (10) then likewise enforces Hermitian symmetry on $\eta(-Q)$ =$\eta(Q)$*. Therefore in this case the reconstructed susceptibility is assumed to be real-valued.

In this derivation, the focal plane of the objective and the front surface of the sample are assumed to coincide (at z=0). This assumption has simplified the preceding analysis and presentation, but it is not required within the scope of the present invention. If the focus is placed below the sample surface by a distance $z_0$, but the delay produced by the reference still coincides with the delay of the sample surface, the data can be modified to account for the displacement. In particular, the modified data $\tilde{D}'(q; k)$ is related to the sampled data $\tilde{D}(q; k)$ by:

$$\tilde{D}'(q;k) = \tilde{D}(q;k)\exp\{iz_0[k-k_z(Mq)]\} \tag{13}$$

This formula can be found by noting that the field relayed by the telescope is now situated at the plane z=$z_0$, adding an extra term $\exp\{-iz_0[k+k_z(q)]\}$ to the right side of Eq. (3). At the same time, the delay reference mirror must be moved a distance further from the beamsplitter so that the new effective delay corresponds to the front surface of the sample, adding a factor of $\exp(-2ikz_0)$ to the right side of Eq. (7) to place the reference delay coincident with the front surface of the sample. Effectively the measured field is computationally propagated at each frequency to the surface of the sample.

Using the mathematical model 146 developed in the foregoing discussion, a solution to the inverse scattering problem may be derived in step 143. In general, the solution is ill-posed and so regularization techniques are used to produce a stable solution. Because the forward problem is linear, we derive a linearized inverse based on least-squares error. To do so, we first specify the complete forward operator K such that D=K$\eta$, which relates the data to the object structure $$\tilde{D}(r;k) = K\eta = \int d^3r' K(r',r;k)\eta(r') \tag{14}$$

where the kernel K(r',r;k) of the operator K is given by $$K(r', r; k) = M^{-1}A(k)^2 \int d^2 r'' \frac{\exp(ik|r'' - r'|)}{|r'' - r'|} P(r/M - r''; k). \tag{15}$$

Given this relation between the data and the object, we can define a least-squares solution $\eta^+$ (r) for object susceptibility as $$\eta^+(r) = \underset{\eta}{\mathrm{argmin}}|D - K\eta|^2 \tag{16}$$

$$= \underset{\eta}{\mathrm{argmin}} \int d^2 r' \int dk |\tilde{D}(r';k) - K\eta(r)|^2.$$

Expressed in operator notation, the solution to this least squares problem is given by the pseudo inverse $\eta^+=(K^\dagger K)^{-1}K^\dagger D$ where $K^\dagger$ is the Hermitian conjugate of K and $K^\dagger K$ is assumed to be invertible. It is much simpler to formulate the least-squares problem in the Fourier domain, using the relation of Eqs. (10) and (11). If we instead define the operator K such that D=K$\tilde{\eta}$. This operator can be used to construct a least squares solution $\tilde{\eta}^+$ such that:

$$\tilde{\eta}^+(Q) = \underset{\tilde{\eta}}{\mathrm{argmin}}(|D - K\tilde{\eta}|^2 + \gamma|\tilde{\eta}|^2) \tag{17}$$

$$= \underset{\tilde{\eta}}{\mathrm{argmin}}\left(\int d^2q \int dk |\tilde{D}(q;k) - \tilde{K}(q;k)\tilde{\eta}\right.$$

$$\{Mq + \hat{z}[k + k_z(Mq)]\}|^2 + \gamma|\tilde{\eta}|\{Mq + \hat{z}[k + k_z(Mq)]\}|^2)$$

with $\tilde{K}(q;k)$ taken from Eq. (11). A Tikhonov regularization term with regularization constant $\gamma$ has been added to stabilize the solution and ensure that a unique solution exists. The solution $\tilde{\eta}^+$ is given in step 144 by $$\tilde{\eta}^+\{Mq + \hat{z}[k + k_z(Mq)]\} = (K^\dagger K + \gamma)^{-1} K^\dagger D \tag{18}$$

$$= \frac{\tilde{D}(q;k)\tilde{K}^*(q;k)}{|\tilde{K}(q;k)|^2 + \gamma}.$$

Resolution and Bandpass of Full-Field ISAM

Eq. (10) expresses a relationship between the 2-D Fourier transform of the data and the 3-D Fourier transform of the object. As mentioned previously, this relationship implies that the resolution of the reconstructed object is space invariant. With suitable specifications of the instrument, it is possible to identify the region of the Fourier space of the structure function that can be sampled. This region is called the "band volume" and is an analogue to the bandlimit of one-dimensional signals, except that the band volume consists of the interior of a shape in three-dimensional Fourier space rather than just a one-dimensional interval.

There are two specifications of the instrument that determine the shape of the band volume. The first is the bandwidth of the illumination, which is specified by the interval of frequencies $k_{min}<k<k_{max}$. The other parameter is the numerical aperture (NA) of the imaging system 0<NA<1. A particular numerical aperture implies a pupil bandpass $$\tilde{P}(q;k)=1 \text{ for } |q| \leq (NA)k$$

$$\tilde{P}(q;k)=0 \text{ for } |q|>(NA)k. \tag{19}$$

These inequalities constrain which points on the data function $\tilde{D}(q;k)$ can be sampled. The relation of Eq. (10) is a one-to-one mapping between each of these points in the data function and points in the 3-D Fourier space of the object $\tilde{\eta}(Q)$. The band volume is the intersection of the volumes defined by the two inequalities expressed in terms of the object spatial frequency Q $$k_{min} < Q^2/(2Q\cdot\hat{z}) < k_{max} \tag{20}$$

$$(2Q\cdot\hat{z})\sqrt{Q^2 - (Q\cdot\hat{z})^2}/Q^2 < NA.$$

Figure 3B:
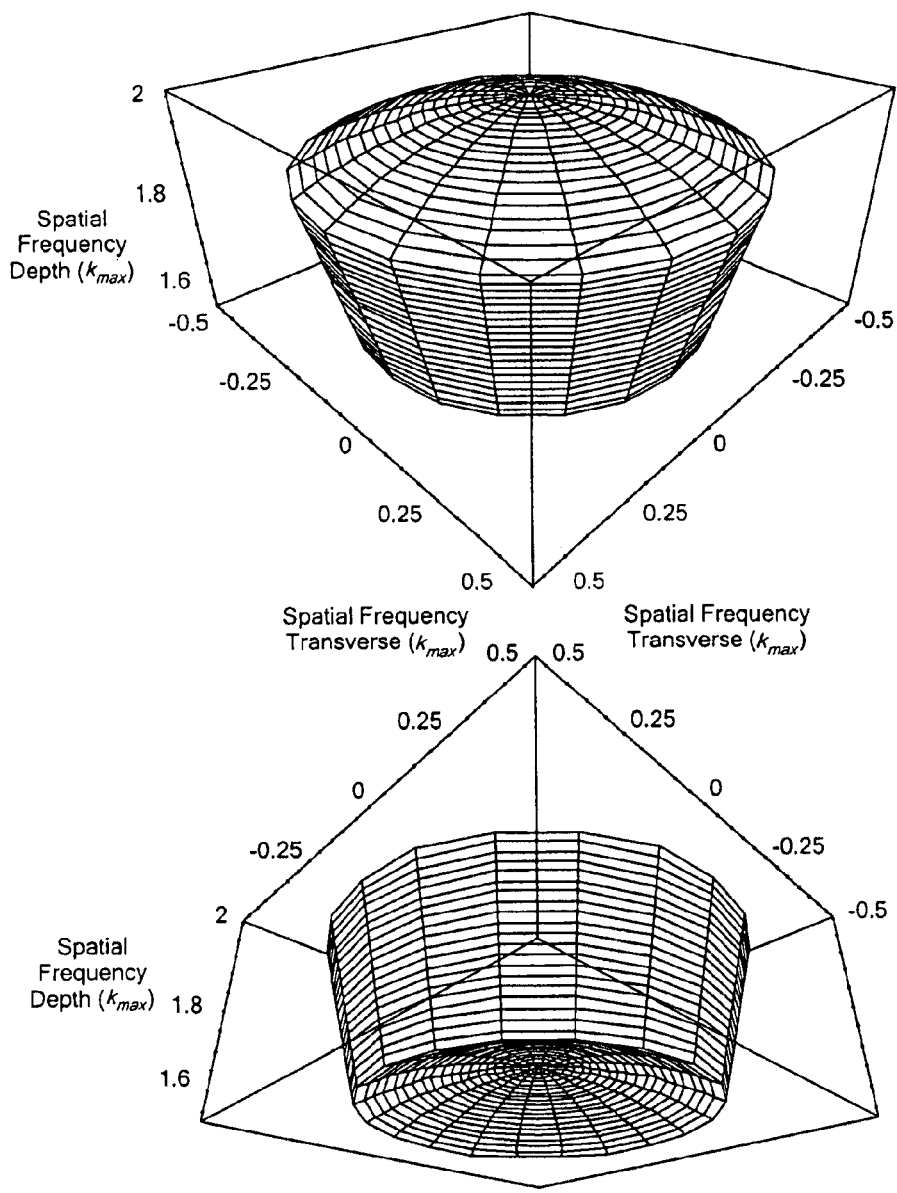
FIG. 3(b) depicts an example of a band volume for an instrument, in accordance with the present invention, having a numerical aperture of 0.5 and bandwidth from 0.8 $k_{max} < k < k_{max}$.
Figure 3C:
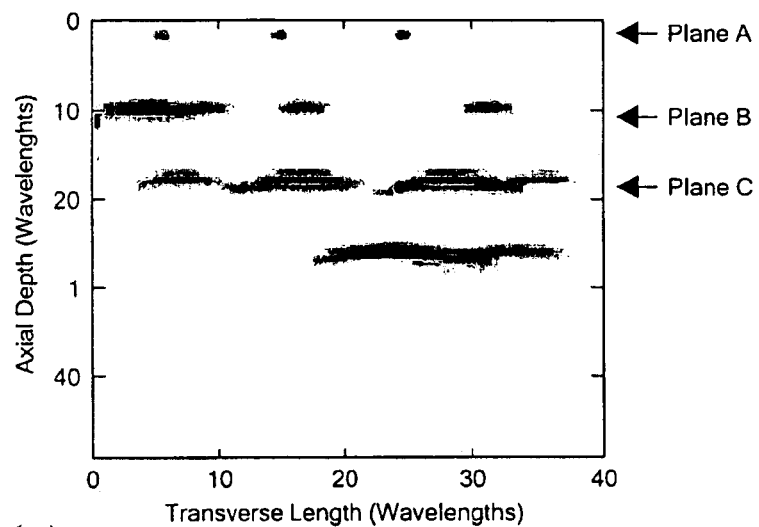
Figure 3D:
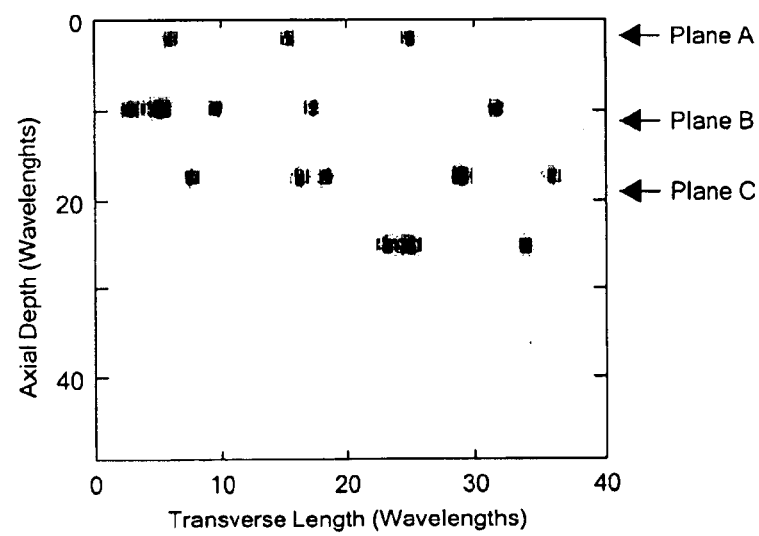
FIG. 3(d) is a projection of the computed reconstruction of the scatterers.

FIG. 3(b) shows an example of a band volume for an instrument with 0.5 NA and bandwidth from 0.8 $k_{max}<k<k_{max}$. The units of the axes are all scaled by $k_{max}$.

There are two views so that the top and bottom surfaces are both visible. The top and bottom surfaces are spherical (with different radii and centers), and the side surface is a right circular cone with its vertex at the origin.

In the limit of small bandwidth and low numerical aperture, the band volume shape approaches that of a circular cylinder. In this limit, the resolution in the axial direction is determined solely by the bandwidth, and the transverse resolution is determined by the numerical aperture, as is normally assumed in OCT. However, the band volume becomes less cylindrical and more cone-shaped as the numerical aperture and bandwidth increase, and axial and transverse resolutions are dependent on both the bandwidth and numerical aperture.

Simulation of Full-Field ISAM

A simulation is now presented to demonstrate inverse scattering in full-field OCT. For purposes of the simulation, an object (element 8 shown in FIG. 3($a$)) is taken as comprising a set of randomly placed point scatterers. The simulated object was imaged with a simulated full-field OCT system, and then the structure of the object was reconstructed from the data. The simulated object volume cross-sectional area was 25 wavelengths in depth, and 40 by 40 wavelengths in the transverse direction. The illumination source had a Gaussian spectrum with a 40% fractional full-width-half-max bandwidth (corresponding, for example, to 320 nm of bandwidth centered at 800 nm). The simulated numerical aperture of the imaging objective was 0.5.

To synthesize the data, first the scattered field $E_s(r';k)$ was calculated using Eq. (2), where the object $\eta(r)$ was a collection of randomly chosen discrete points. From this, a two-dimensional Fourier transform computed $\tilde{E}_s(q;k)$. Then the synthesized data function was calculated by $\tilde{D}(q;k)=A(k)\tilde{E}_s(q;k)\tilde{P}(q;k)$. Finally, a two-dimensional inverse Fourier transform yielded $D(r';k)$. Eq. (10) was deliberately not used to compute the data because using an alternate and more direct method of computing the data provided a better test of the inverse scattering method.

FIG. 3($c$) shows the projection of the simulated data collapsed (summed) along one transverse direction. The units are in terms of the center wavelength. Instead of showing the Fourier-transformed function $\tilde{D}(r;k)$ itself, which would be difficult to interpret if it was plotted directly, we show the inverse Fourier transform of $\tilde{D}(r;k)$ with respect to k. It is the data on the focal plane array that would be observed if the delay $\tau$ were scanned, rather than the frequency k, which is given by the intensity function of Eq. (12). The focus is on the top surface at zero depth, which also corresponds to zero delay. As can be seen, as the delay is increased from zero, the diffracted images of the point scatterers become increasingly large. This corresponds to the standard degradation in resolution one expects from defocus when inverse scattering is not used.

To compute the image estimate $\eta^+(r)$ from the synthetic data $D(r; k)$, first $D(q;k)$ was computed using the two-dimensional Fourier transform. Next, Eq. (18) was used to compute $\tilde{\eta}^+\{q+\hat{z}[k+k_z(q)]\}$. However, in practice to find $\eta^+(r)$ from $\tilde{\eta}^+(Q)$ numerically, one would likely use the three-dimensional inverse discrete Fourier transform. Unfortunately, Eq. (18) does not specify $\tilde{\eta}^+$ in a form to which the inverse discrete Fourier transform can be readily applied, because it is a function of the more complicated argument $q+\hat{z}[k+k_z(q)]$. In practice, this means that the discrete sampling of the function $\tilde{\eta}^+$ is uniform in the variables q and k and not in Q to which the inverse Fourier transform can be directly applied. By using an interpolator, one can compute the samples of $\tilde{\eta}^+$ on points that are uniform in Q from existing samples of $\tilde{\eta}^+\{q+\hat{z}[k+k_z(q)]\}$ In this simulation, a one-dimensional cubic B-spline interpolator was used to interpolate from the coordinates $q+\hat{z}[k+k_z(q)]$ to Q. Because only the $\hat{z}$ coordinate is not sampled uniformly, the resampling only needs to occur along this direction.

Finally, after taking the three-dimensional inverse Fourier transform of $\tilde{\eta}^+(Q)$, the reconstruction $\eta^+(r)$ results, which is shown in FIG. 3($d$). As can be seen, the reconstruction corrects for the diffraction of the data, and produces point-like images. FIG. 4 shows three en face planes corresponding to the depths A, B, and C marked in FIG. 3($c$). The left column is the time-domain data measured in each of the en face planes, and the right column is the image of the scatterers computed by inverse scattering. Planes that are further from the focus have more diffuse images when viewed in the raw data because of the effect of defocus. One can also see the interference between the images of adjacent scatterers. Despite the interference between scatterers, each point is clearly resolved with space-invariant resolution in the reconstructed image. This shows the algorithm correctly separates the interference patterns from scatterers to produce high resolution images.

Figure 5A:
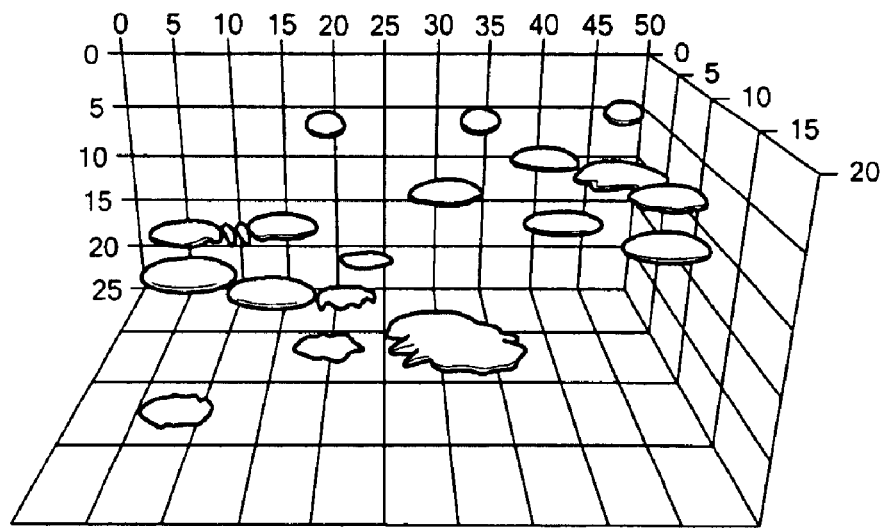
FIG. 5(a) compares a volume isosurface plot of the raw data with the reconstructed computed image of FIG. 5(b).
Figure 5B:
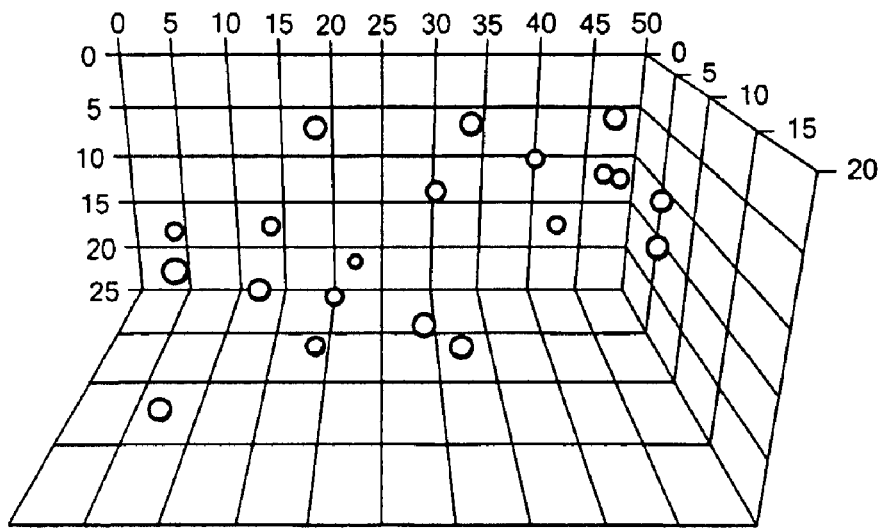

To show the overall improvement to the data, FIG. 5($a$) is a volume isosurface plot of the raw data, while the reconstructed computed image is shown in FIG. 5($b$). Again, the blurring of the data is increasingly apparent with increasing distance from the focus plane at the top of the volume. In addition, stripe-like features can be seen for the isosurfaces corresponding to interfering scatterers. This method can correct for the diffraction effects and produce point-like images in FIG. 5($b$) for each of the scatterers. The planes of the scatterers need not be so widely separated for the algorithm to distinguish them, but was deliberately done to make the diffraction effects easier to visualize.

There is an important difference in the reconstructions of full-field OCT and conventional scanned beam OCT. In conventional scanned beam OCT, it has been shown by Ralston et al., *Inverse Scattering for Optical Coherence Tomography, J. Opt. Soc. Am. A*, vol. 23, pp. 1027-1037, (2006), incorporated herein by reference, that the magnitude of the signal captured from scatterers away from the focus is inversely proportional to the distance from the focus. In practice this places a limit on the axial range of the sample that can be imaged before the signal-to-noise ratio becomes unacceptable. However, there is no such attenuation of the signal away from the focus in the full-field OCT case. The practical limit to the depth of full-field OCT is determined by vignetting of the relayed field inside the relay telescope, and the scattering of the sample. However, this advantage may be offset because full-field OCT may be less able to discriminate between single scattering and multiply scattered photons due to its multimode detection.

Transverse-Scanned Focused Gaussian Beam Implementation

Figure 6:
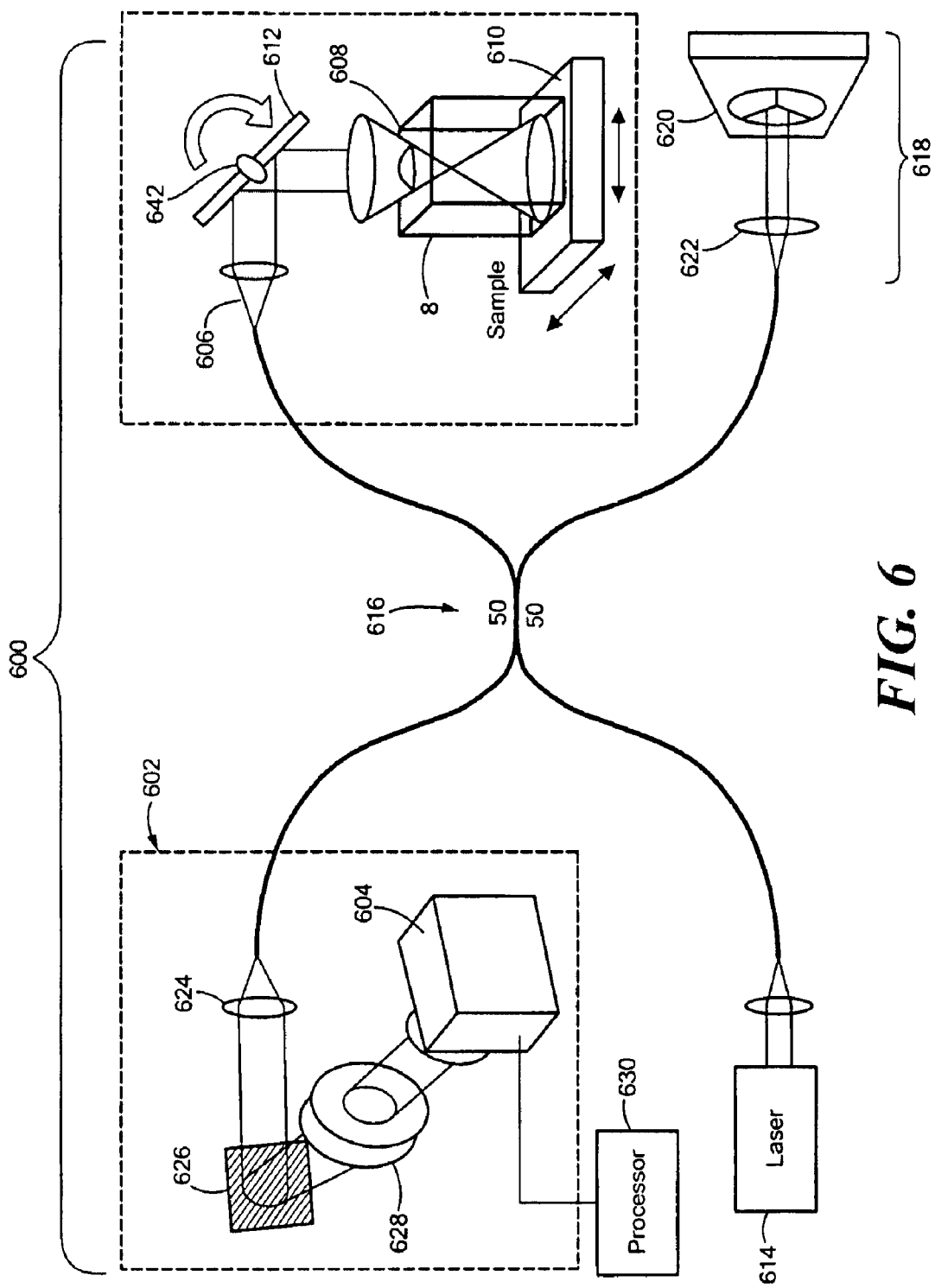
FIG. 6 is a schematic depiction of an interferometric synthetic aperture microscope using spectral detection in accordance with an embodiment of the present invention.

Preferred embodiments of the present invention implement computed interferometric imaging by employing a fiber-optic Michelson interferometer 600 seeded by a source of femtosecond pulses, as now described with reference to FIG. 6. A spectral interferometer, designated generally by numeral 602, measures the interferometric cross-correlation between a fixed-delay reference pulse and a pulse reflected back from a sample 8. The measured spectrum on a line camera 604 corresponds to the Fourier transform of the cross-correlation signal, from which the amplitude and phase of the reflected field from the sample are inferred. The sample probe beam 606 is focused by a microscope objective 608 so that the beam focus is at a fixed distance inside the sample. At each position of the beam, the spectral interferogram of the backscattered optical field is measured. The beam is laterally translated in two-dimensions through the sample by moving a stage 610 or by steering the beam with a pair of galvanometer-driven mirrors 612 before entering the objective.

Measurements are made using a femtosecond spectral interferometer 600. Fourier-domain, or frequency-swept, OCT, has been described by Choma et al., *Sensitivity advantage of swept source and Fourier domain optical coherence tomography, Opt. Exr.*, vol. 111, pp. 2183-89 (2003), which is incorporated herein by reference. A femtosecond laser 614 (such as supplied by Kapteyn-Murnane Laboratories of Boulder, Colo.) delivers ultrashort pulses to provide broadband illumination for the system. In one embodiment of the invention, the center wavelength of the source is 800 nm, with a bandwidth of 100 nm. These first-order field quantities fluctuate too rapidly to be detected directly, thus an optical fiber-based Michelson interferometer is incorporated. The illumination is divided by a 50:50 fiber-optic coupler (splitter) 616 between a reference arm 618 containing a delay mirror 620 and a sample arm that contains a lens (objective) 622 to focus the Gaussian beam into the sample 8. Light returns from the sample and reference arms and is directed into spectrometer 602. In the spectrometer, the light is collimated with an achromatic lens 624 and dispersed off of a blazed gold diffraction grating 626, which, in one embodiment, has 830.3 grooves per millimeter and a blaze angle of 19.70 degrees for a blaze wavelength of 828 nm. To reduce lens aberrations, the dispersed optical spectrum is focused using a pair of achromatic lenses 628. The focused light is incident upon a line-scan camera (L104k-2k, Basler, Inc.) 604 which contains a 2048-element charge-coupled device (CCD) array with 10×10 pm detection elements. Camera 604 operates at a maximum readout rate of over 29 kHz, thus one axial scan can be captured during an exposure interval of about 34 μs. The data is sent to processor 630 which may also govern operation of a galvanometric controller 642 and receive a trigger derived therefrom in order to activate frame acquisition, for example.

We obtain a mathematical model of interferometric synthetic aperture microscopy (ISAM) by considering the propagation of the focused beam from the objective into the sample (into some volume V), scattering within the sample (in the first Born approximation), the propagation of the scattered light back into the objective (over some surface Σ), and the measurement of the cross-correlation with the reference pulse. The expression that models these steps (17) is given by $$S(r_o,k)=A(k)\int_\Sigma d^2r\int_V d^3r'G(r',r,k)g(r'-r_o,k)\eta(r')g(r-r_o,k) \quad (21)$$

where k is the wave number of the illumination, $r_0$ is the transverse position of the Gaussian beam, g describes the normalized Gaussian beam profile, $A^2(k)$ is the power spectral density of the source, G is the Green function, and η is the susceptibility of the sample. The normalized beam profile is given by $g(r,k)=W^{-2}(k)e^{-r^2/2W^2(k)}/2\pi$, where $W(k)=\alpha/k$, $\alpha=\pi/$NA, and NA is the numerical aperture of the beam. The Green function is given by $G(r',r,k)=e^{ik(r-r')}/|r-r'|$. After two-dimensional (2-D) Fourier transformation with respect to $r_0$, and further manipulation, the 2-D Fourier transform of the signal is given by the expression $$\tilde{S}(Q,k) = A(k)\int d^2q \int dz' \frac{i2\pi}{k_z(q)} e^{ik_z(q)(z'-z_0)} \qquad (22)$$
$$\tilde{g}_0(q,k)e^{ik_z(Q-q)(z'-z_0)}\tilde{g}_0(Q-q,k)\tilde{\eta}(Q;z'),$$

where $k_z(q)=\sqrt{k^2-a^2}$, $z_0$ is the position of the beam focus, $\tilde{\eta}(Q,z')$ is the 2-D transverse Fourier transform of the susceptibility, and $\tilde{g}_0(q,k)=e^{-q^2\alpha^2/2k^2}$ is the 2-D Fourier transform for the beam profile g(r,k) in the waist plane of the beam. After the expression for $\tilde{g}_0$ is substituted into Eq. (22), and an asymptotic expansion of $\tilde{S}$ is made for large $\alpha^2$, this relationship reduces to $$\tilde{S}(Q,k) = A(k)\left(\frac{i2\pi^2}{k_z(Q/2)}\frac{k^2}{\alpha^2}e^{-2ik_z(Q/2)z_0}e^{-\frac{\alpha^2 Q^2}{4k^2}}\right)\tilde{\tilde{\eta}}(Q;-2k_z(Q/2)), \qquad (23)$$

where $\tilde{\tilde{\eta}}$ is the 3-D Fourier transform of η, i.e. the one dimensional Fourier transform of $\tilde{\eta}(Q;z)$ with respect to z. This expansion is valid even when NA≈1 because $\alpha^2$ is sufficiently large for the first term of the expansion to dominate. Eq. (23) relates the 3-D Fourier transform of the object susceptibility to the 2-D Fourier transform of the signal. Implicit in this formula is a diagonal linear integral operator in the 3-D Fourier space of the susceptibility, and so the achievable resolution is spatially-invariant and does not depend on the proximity to the focus.

Because of the simple relationship between the susceptibility and the signal, ISAM can be implemented efficiently by resampling or interpolating the data in a manner analogous to the numerical implementation of the Fourier projection slice theorem, as described in Natterer, *The Radon Transform*, (Wiley, 1986, incorporated herein by reference) and as used in x-ray computed tomography or synthetic aperture radar (SAR), but the resampling grid for ISAM is hyperbolic rather than polar. In addition, since Eq. (23) is a multiplicative (or diagonal) form, generalization to a regularized inverse method such as Tikhonov regularization (Tikhonov, *Dokl. Akad. Nauk SSR*, vol. 39, p. 195, 1943) is straightforward.

Regardless of the type of detection used, the beam orientation is fixed while the axis is translated over the sample on a Cartesian grid in directions orthogonal to the beam axis and subsequent axial scans are displayed on adjacent lines to form a tomogram. Suppose the beam is generated by light emerging from an optical fiber and then propagating through a lens to form a focused beam incident on the sample. With the axis of the fiber passing through the point $r_0$ in the z=0 plane and with the waist plane of the focused field at $z=z_0$, the incident field may be described by the power spectrum $|A(k)|^2$ and a normalized mode g such that $$U_1(r;r_0,k)=A(k)g(r-r_0). \qquad (24)$$

The beam may be described in a plane wave decomposition, $$g(r-r_0,k) = \frac{1}{(2\pi)^2}\int d^2q e^{iq\cdot(r-r_0)}e^{ik_z(q)(z-z_0)}\tilde{g}_0(q,k), \qquad (25)$$

where $\tilde{g}_0$ is the two dimensional Fourier transform of g in the $z=z_0$ plane, and the dispersion relation is given by $k_z=\sqrt{k^2-q^2}$. The beam waist is assumed to depend on the wave number, as $W_0(k)=\alpha/k$ where $\alpha=\pi/NA$ and NA is the numerical aperture of the output lens. Thus $$\tilde{g}_0(q,k) = e^{-q^2 W_0^2/2} = e^{-q^2\alpha^2/(2k^2)}. \tag{26}$$

The scattered field, within the first Born approximation, is given by $$U_s(r,r_0,k) = \int d^3r' G(r',r,k) U_1(r',r_0,k)\eta(r'). \tag{27}$$

Making use of the expressions above for the incident field, $$U_s(r,r_0,k) = A(k) \int d^3r' G(r',r,k) g(r'-r_0,k)\eta(r'). \tag{28}$$

The signal coupled back in to the fiber is given by the projection of the backscattered field onto the fiber mode g at the exit plane of the fiber. Thus $$S(r_0,k) = \int_{z=0} d^2r U(r,r_0,k) g(r-r_0,k), \tag{29}$$

which becomes $$S(r_0,k) = A(k) \int_{z=0} d^2r \int d^3r' G(r',r,k) g(r'-r_0,k) g(r-r_0,k)\eta(r'). \tag{30}$$

The Green function for free-space is given by the angular spectrum $$G(r', r, k) = \frac{i}{2\pi} \int d^2q e^{iq\cdot(r-r')} \frac{e^{-ik_z(q)(z-z')}}{k_z(q)}, \tag{31}$$

where it is assumed that the scatterers are all located such that z<z' for the whole support of the scatterers. Making use of this expression and Eq. (30), it may be seen that the two-dimensional Fourier transform of S with respect to $r_0$ is given by the expression $$\tilde{S}(Q, k) = i2\pi A(k) \int d^2q \int dz' \frac{1}{k_z(q)} e^{ik_z(q)(z'-z_0)} \tag{32}$$

$$e^{ik_z(q-Q)(z'-z_0)} e^{-\frac{\alpha^2 q^2}{2k^2}} e^{-\frac{\alpha^2|q-Q|^2}{2k^2}} \tilde{\eta}(Q, z').$$

This equation may be solved for $\eta$ by blunt numerical methods. Such methods are numerically expensive. An analytic result may be obtained by considering the shifted form of the integral $$\tilde{S}(Q, k) = i2\pi A(k) \int d^2q \int dz' \frac{1}{k_z(q)} e^{ik_z(q)(z'-z_0)} \tag{33}$$

$$e^{ik_z(q-Q)(z'-z_0)} e^{-\frac{\alpha^2 Q^2}{4k^2}} e^{-\frac{\alpha^2|q-Q/2|^2}{k^2}} \tilde{\eta}(Q, z').$$

For large values of $\alpha$ this integral may be evaluated asymptotically. The integrand, modulo the Gaussian, may be expanded in a Taylor series around the point $q=Q/2$, $$\frac{e^{i[k_z(q)+k_z(q-Q/2)](z_0-z')}}{k_z(q)} = \tag{34}$$

$$\left. \frac{e^{2ik_z(Q/2)(z'-z_0)}}{k_z(Q/2)} + q\cdot\nabla_q \frac{e^{i[k_z(q)+k_z(q-Q/2)](z_0-z')}}{k_z(q)}\right|_{q=Q/2} + \ldots$$

Replacing this part of the integrand, the leading term is given by an integral over the constant term in the Taylor expansion:

$$\tilde{S}(Q, k) = \tag{35}$$

$$i2\pi A(k) e^{-\frac{\alpha^2 Q^2}{4k^2}} \int dz' \frac{e^{2ik_z(Q/2)(z'-z_0)}}{k_z(Q/2)} \int d^2q e^{-\frac{\alpha^2|q-Q/2|^2}{k^2}} \tilde{\eta}(Q, z').$$

The Gaussian integral may be easily carried out and the remaining integral is seen to be a Fourier transform with respect to z', $$\tilde{S}(Q, k) = \frac{k^2}{\alpha^2} i2\pi^2 A(k) \frac{e^{-2ik_z(Q/2)z_0}}{k_z(Q/2)} e^{-\frac{\alpha^2 Q^2}{4k^2}} \tilde{\tilde{\eta}}[Q, -2k_z(Q/2)], \tag{36}$$

where $\tilde{\tilde{\eta}}$ is the three-dimensional Fourier transform of $\eta$. The next term in the expansion yields a contribution proportional to $\alpha^{-4}$. In the extreme limit that NA→1, it may be seen that $\alpha \to \pi$ so that we expect the leading term approximation to be sufficient even in the case of high numerical aperture. It might be noted that this expansion is distinct from the paraxial approximation (essentially a small |q| expansion of $k_z(q)$) which fails as NA→1. Eq. (36) expresses a resampling scheme illustrated in FIG. 1. To find an appropriate regularization scheme, we will write $$\tilde{S}(Q, k) = \int d\beta H(Q, k, \beta) \tilde{\tilde{\eta}}(Q, \beta), \tag{37}$$

where $$H(Q, k, \beta) = \frac{k^2}{\alpha^2} i2\pi^2 A(k) \frac{e^{-2ik_z(Q/2)z_0}}{k_z(Q/2)} e^{-\frac{\alpha^2 Q^2}{4k^2}} \delta[\beta + 2k_z(Q/2)] \tag{38}$$

$$\equiv f(Q, k, \beta)\delta[\beta + 2k_z(Q/2)].$$

Then the kernel of the normal operator is given by the expression $$H^*H(Q, \beta, \beta') \equiv \tag{39}$$

$$|f(Q, 1/2\sqrt{\beta^2+Q^2}, \beta)|^2 \frac{\beta}{2\sqrt{\beta^2+Q^2}} \delta(\beta-\beta').$$

And the kernel of the Tikhonov regularized psuedo-inverse, with white noise N is given by the expression $$H^+(Q, k; \beta) = \frac{f^*(Q, k, \beta)\delta(k-1/2\sqrt{\beta^2+Q^2})}{|f(Q, k, \beta)|^2 + 2Nk/k_z(Q/2)}. \tag{40}$$

The object structure is then given by $$\tilde{\tilde{\eta}}^+(Q, \beta) = \left[\frac{f^*(Q, k, \beta)\tilde{S}(Q, k)}{|f(Q, k, \beta)|^2 + 2Nk/k_z(Q/2)}\right]_{k=\frac{1}{2}\sqrt{\beta^2+Q^2}} \tag{41}$$

The object structure in the coordinate domain is obtained by applying the three-dimensional inverse Fourier transform.

To achieve phase stability of the signal, a microscope coverslip (not shown) may be placed on top of sample 8 and the top reflection from the air-coverslip interface acts as a fixed reference delay relative to the object. The delay fluctuations of the interferometer are removed from each cross-correlation interferogram by locating the air-coverslip reflection in each interferogram, estimating the phase and group delay of the reflection, and applying the opposite phase and group delay to the entire interferogram. Prior to processing, the spectra, each representing a column of depth-dependent data, are assembled adjacently as the beam is transversely scanned over the sample. The detected digital signal is interpolated to account for the non-uniform sampling of the spectrum and to compensate for up to third-order dispersion. Specifically, the signal is interpolated by a factor of two by a band-limiting interpolator implemented using the fast Fourier transform (FFT). This prepares the signal for the cubic B-spline interpolation, which has a transfer function with an amplitude that attenuates frequencies close to the Nyquist limit. The cubic B-spline interpolator resamples the spectrum to a uniform frequency space according to a calibration procedure utilizing a single reflector placed at the focus of the objective lens. Sample movement, inducing phase and group delay changes, is tracked using a reference microscope coverslip, and the deviations are corrected. At this point, the quantity $S(r_0, k)$, in Eq. (1) has been estimated. Next, the two-dimensional FFT in the transverse directions is calculated to yield $\tilde{S}(Q,k)$. Then, the non-uniform ISAM resampling and filtering of Eq. (3) using cubic B-splines is implemented to yield $\tilde{\eta}$. Finally, the 3-D inverse FFT is used to attain the ISAM reconstruction, an estimate of $\eta(r)$.

By application of ISAM techniques as described, in vivo imaging may advantageously be performed on larger volumes of tissue than volumes that would otherwise have to be resected. Furthermore, ISAM achieves high-speed, high-resolution imagery without need for the timely processing, sectioning, and staining of a resection.

With the use of near-infrared light, high-resolution ISAM facilitates the noninvasive monitoring of cellular and nuclear development with penetration depths up to 3 mm. Of course, in regions of extreme scattering or absorption penetration depths may be reduced.

Image formation algorithms are characterized differently than image post-processing routines. In particular, ISAM is a unique image formation method that utilizes the fundamental resolution capabilities of the acquired optical signal based on the physics of the scattering within the detection beam. In contrast, a simple image post-processing algorithm may attempt to extrapolate beyond the information inherent an image. For example, maximum likelihood, blind-deconvolution, or entropy-constrained algorithms can effectively produce energy compaction as an estimated solution to an image reconstruction. Such estimation may incorrectly reconstruct features in an image, thus misrepresenting the true biological structure and potentially leading to an incorrect diagnosis. ISAM is not based on estimation, thus such misrepresentations do not exist. Furthermore, estimation algorithms often exceed the limited computational complexity necessary for real-time imaging. The ISAM image formation algorithm can be implemented with computational complexity of O(NlogN), where N is the number of volume elements to resolve, which makes ISAM amenable to real-time imaging. Furthermore, the ISAM algorithm can be applied to planes as well as volumes, thus enhancing cross-sectional imaging.

Azimuthally-Scanned Implementation

Embodiments of the invention are now described in which a focused beam is directed perpendicular to an OCT catheter, which might, for example, be incorporated into an endoscope. An endoscope, used for exploring the tubular lumens within the human gastrointestinal tract, typically consists of a long, flexible device of 1 cm diameter or less. Inside the endoscope, in addition to a source of white light illumination and optics for imaging, for example, on a charge-coupled device (CCD) detector, are working channels through which various instruments for biopsy or manipulating tissue are passed. For example, tissue biopsy samples can be extracted and withdrawn by forceps or suction. Smaller diameter catheters are used in the cardiovascular system, e.g. for the insertion of balloons for angioplasty or to deploy stents. Intravascular catheters minimize invasiveness and provide access to vascular lesions associated with cardiovascular disease.

An azimuthally-scanned OCT system would typically include a working channel containing a single-mode optical fiber, a focusing lens (typically a graded index lens cemented or fused to the fiber), and a right-angle prism or a custom cleaved surface for reflecting the beam by 90 degrees to the side of the catheter.

Fiber-optic OCT catheters have been integrated with endoscopes to image the esophagus, colon, and other internal organs and mucosal tissue, as described, for example, by Tearney et al., *In vivo endoscopic optical biopsy with optical coherence tomography, Science*, vol. 276, pp. 2037-39 (1997), incorporated herein by reference. In instruments based on fiber-optic OCT, the illumination originates inside the object or tubular lumen being imaged, and is usually scanned azimuthally around the long axis of the catheter. As the catheter is azimuthally scanned and translated along the long-axis of the catheter, a 3-D image of the object is acquired. Because the beam is typically focused at a fixed distance from the catheter, the depth-of-focus of the resulting images is confined to a narrow annulus.

By rotating the catheter about its long-axis, the beam may be directed along any path perpendicular to the axis. By pushing or pulling the catheter, the beam is translated along the long-axis of the catheter. Together these two degrees of freedom enable the instrument to scan a cylindrically shaped volume around the catheter. Typical imaging with this catheter design involves acquisition of axial scans (either in the time or frequency domain) while rotating the catheter through 360 degrees, advancing the catheter a small distance along its long-axis, and repeating the measurement. After acquisition, one possesses a data set parameterized by the illumination frequency (or time delay), the angular coordinate of the catheter during the scan, and the translational position of the catheter along its axis. With our solution of the inverse problem, we infer the object susceptibility from these data.

An algorithm that infers the susceptibility of a scatterer from the signal acquired in angularly scanned OCT is now described. These may be advantageously employed in catheter-based optical coherence tomography, but the scope of the present invention is not limited and may include application in endoscopic or intravascular ultrasound as well. Other applications may include acoustic, sonar, and seismic sensing where the imaged object is close to a focused transducer, and radar sensing of objects near a rotating dish antenna.

The Forward Problem for Azimuthally-Scanned ISAM

In contradistinction to the forgoing discussion wherein the illuminating Gaussian beam was translated in a straight line perpendicular to its axis, in the following discussion, rotation of the Gaussian beam is considered about the origin.

We consider an experiment in which a Gaussian beam originates at a position with Cartesian coordinates (0, p, 0). Let us denote Cartesian coordinates fixed relative to the sample by r=(x, y, z) and let us denote Cartesian coordinates fixed relative to the beam by r'=(x', y', z'). For each fixed axial position of the fiber y=y'=p. The beam is directed at an angle θ from the z-axis, and along the z' axis. The coordinates may be related by a rotation matrix R(θ) so that r=R(θ)r' where $$R(\theta) = \begin{pmatrix} \cos\theta & 0 & \sin\theta \\ 0 & 1 & 0 \\ -\sin\theta & 0 & \cos\theta \end{pmatrix}. \quad (42)$$

Figure 7:
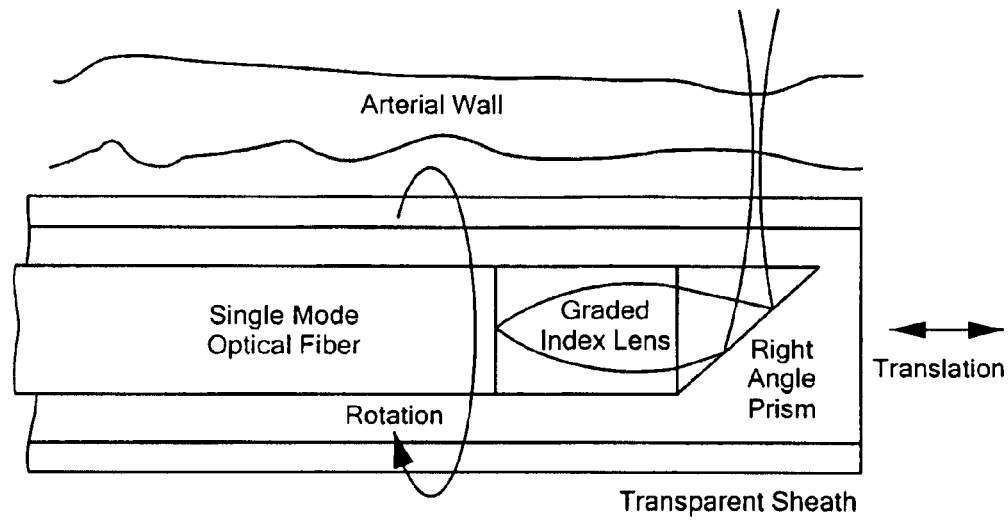
FIG. 7 is a schematic view of an OCT catheter shown in cross-section.
Figure 8:
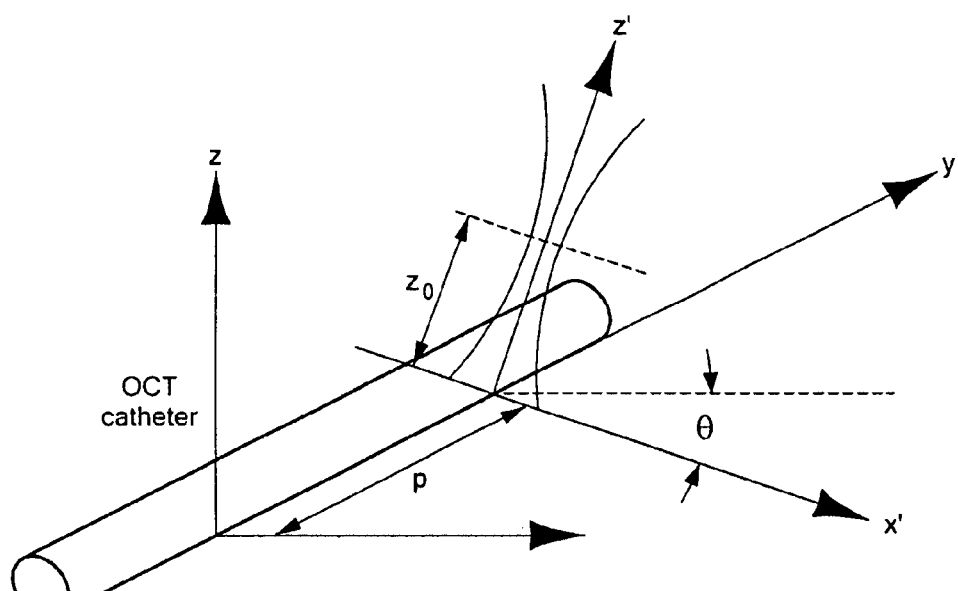
FIG. 8 defines the coordinates used in the description of the OCT catheter.

The beam is focused a distance $z_0$ from the y axis. The field is polychromatic with power spectrum $A^2(k)$ where $k=\omega/c$ is the wave number associated with frequency $\omega$. The width of the beam waist is a function of frequency given by $W(k)=\alpha/k$, where $\alpha=\pi/NA$, and NA, as above, is the numerical aperture of the focused beam. The beam is rotationally scanned so that the signal is sampled for all angles $-\pi \leq \theta < \pi$, and the beam is also translated along the y axis to cover all axial coordinates p. FIG. 7 illustrates this notation.

In the discussion above, it was assumed that the direction of propagation of the beam was fixed to be along the z direction. The location of the center of the beam in the waist plane was given by $r_0$. Then the signal measured in the interferometer is given by the expression $\tilde{S}(r,k)$, which is given by $$\tilde{S}(r,k) = i(2\pi)^{-2}A(k)k^{-1}\int_V d^3 r\eta(r)f^2(r-r_0;k), \quad (43)$$

Where $\eta(r)$ is the susceptibility of the sample being probed, $f^2(r';k)$ is given by the expression:

$$f^2(r';k) = \frac{1}{(2\pi)^2}\int d^2\xi \exp(-i\xi\cdot r')\frac{1}{2}\left(\frac{\alpha^2}{k^2} + \frac{i(z'-z_0)}{k}\right)^{-1} \quad (44)$$

$$\exp\left(-\frac{\xi^2\alpha^2}{4k^2}\right)\exp\left[i(z'-z_0)\sqrt{(2k)^2-\xi^2}\right]$$

where $\xi=(\xi_x,\xi_y,0)$ and the integral is over the $\xi_x$, $\xi_y$ plane. Note that we do not now make the paraxial approximation for the phase term. The signal depends on frequency, position along the y-axis, and the angle of propagation of the beam as described above. This signal, $\tilde{S}(k,p,\theta)$, may be found from Eq. (39) by writing the integrand in the coordinates stationary with respect to the beam. Thus we obtain $$\tilde{S}(k,p,\theta) = i(2\pi)^{-2}A(k)k^{-1}\int_V d^3 r' \eta[R(\theta)r']f^2(r'-p\hat{y};k). \quad (45)$$

By substituting Eq. (44) into Eq. (45) and rearranging terms, we find $$\tilde{S}(k,p,\theta) = \frac{i}{2}A(k)k^{-1}\int d^2\xi \exp\left[-iz_0\sqrt{(2k)^2-\xi^2}\right]\exp\left(-\frac{\xi^2\alpha^2}{4k^2}\right) \quad (46)$$

-continued
$$\int d^3 r' \exp[-i\xi\cdot(r'-p\hat{y})]\eta[R(\theta)r']$$

$$\left[\frac{\alpha^2}{k^2} + \frac{i(z'-z_0)}{k}\right]^{-1}\exp\left[iz'\sqrt{(2k)^2-\xi^2}\right].$$

In our analysis of the OCT inverse problem on a Cartesian grid, we found that under certain reasonable approximations, the data could be related to the object susceptibility through a resampling scheme in the Fourier domain. We derive a similar relation here. To do so, it will be advantageous to replace $$\left[\frac{\alpha^2}{k^2} + \frac{i(z'-z_0)}{k}\right]$$

with an approximation commensurate with the natural geometry of the problem. Explicitly, we replace z' with $\rho'=\sqrt{z'^2+x'^2}$. For most OCT systems, the bandwidth is a small fraction of the central frequency and so we replace $$\frac{1}{k^2} \text{ with } \frac{1}{kk_0}.$$

Thus the factor $$\left[\frac{\alpha^2}{k^2} + \frac{i(z'-z_0)}{k}\right]$$

is replaced by $$\frac{1}{k}\left[\frac{\alpha^2}{k_0} + i\left(\sqrt{x'^2+z'^2}-z_0\right)\right].$$

This expression is slowly varying relative to the rapidly varying phase of the term $\exp[iz'\sqrt{(2k)^2-\xi^2}]$, and so approximations to it tend not to change the result greatly. With this substitution, $$\tilde{S}(k,p,\theta) = \frac{i}{2}A(k)\int d^2\xi \exp\left[-iz_0\sqrt{(2k)^2-\xi^2}\right]\exp\left(-\frac{\xi^2\alpha^2}{4k^2}\right) \quad (47)$$

$$\int d^3 r' \exp[-i\xi\cdot(r'-p\hat{y})]\eta[R(\theta)r']\left[\frac{\alpha^2}{k_0}+i(\rho'-z_0)\right]^{-1}$$

$$\exp\left[iz'\sqrt{(2k)^2-\xi^2}\right].$$

To evaluate this integral, we change variables in the inner integral to the coordinates stationary in the reference frame of the sample, $$\tilde{S}(k,p,\theta) = \quad (48)$$

-continued $$\frac{i}{2}A(k)\int d^2\xi \exp\left[-iz_0\sqrt{\frac{(2k)^2-}{\xi^2}}\right]\exp\left(-\frac{\xi^2\alpha^2}{4k^2}\right)\exp(i\xi_y p)$$

$$\int d^3r \exp\left\{-i\left[\xi-\hat{z}\sqrt{(2k)^2-\xi^2}\right]\cdot R[(-\theta)r]\right\}\eta(r)\left[\frac{\alpha^2}{k_0}+i(\rho-z_0)\right]^{-1},$$

where $\rho=\rho'=\sqrt{x^2+z^2}$. It may be seen that the integral over r results in a Fourier transform if we note that $\lfloor\xi-\hat{z}\sqrt{(2k)^2-\xi^2}\rfloor\cdot R(-\theta)r=R(\theta)\lfloor\xi-\hat{z}\sqrt{(2k)^2-\xi^2}\rfloor\cdot r$, after which we obtain $$\tilde{S}(k,p,\theta)= \tag{49}$$

$$\frac{i}{2}A(k)\int d^2\xi \exp\left[iz_0\sqrt{(2k)^2-\xi^2}\right]\exp\left(-\frac{\xi^2\alpha^2}{4k^2}\right)\exp(i\xi_y p)$$

$$\tilde{\eta}\left\{-R(\theta)\left[\xi-\hat{z}\sqrt{(2k)^2-\xi^2}\right]\right\}$$

where $\tilde{\eta}(\beta)$ is the weighted Fourier transform of $\eta(r)$ given by $$\eta(\beta)=\int d^3r \exp(ir\cdot\beta)\eta(r)\left[\frac{\alpha^2}{k_0}+i(\rho-z_0)\right]^{-1}. \tag{50}$$

To change the integral over $\xi$ to a cyclic convolution, we make the substitution $\sqrt{(2k)^2-\xi_y^2}\cos\phi=\xi_x$ so that $\sqrt{(2k)^2-\xi_y^2}\sin\phi=\sqrt{(2k)^2-\xi^2}$, after which we obtain $$\tilde{S}(k,p,\theta)=\frac{i}{2}A(k)\int d\xi_y \exp(i\xi_y p) \tag{51}$$

$$\int_0^\pi d\phi\left\{\left[\sqrt{(2k)^2-\xi_y^2}\sin\phi\right]\exp\left[-iz_0\sqrt{\frac{(2k)^2-}{\xi^2}}\right]\exp\left(-\frac{\xi^2\alpha^2}{4k^2}\right)\right\}$$

$$\tilde{\eta}\left\{-R(\theta)\left[\hat{x}\cos\phi\sqrt{(2k)^2-\xi_y^2}+\hat{y}\xi_y-\hat{z}\sin\phi\sqrt{(2k)^2-\xi_y^2}\right]\right\}.$$

For brevity, we define the kernel function $K(k,\xi_y,\phi)$.

$$K(k,\xi_y,\phi)= \tag{52}$$

$$\frac{i}{2}A(k)\left[\sqrt{(2k)^2-\xi_y^2}\sin\phi\right]\exp\left[-iz_0\sqrt{(2k)^2-\xi^2}\right]\exp\left(-\frac{\xi^2\alpha^2}{4k^2}\right).$$

We note that the $\cos\phi$ next to x and the $\sin\phi$ next to $\hat{z}$ in Eq. (51) effect a rotation in the x-z plane through an angle $-\phi$ of a vector $x\sqrt{(2k)^2-\xi_y^2}$. Given this, we can express Eq. (51) as a cyclic convolution:

$$\tilde{S}(k,p,\theta)=\int d\xi_y \exp(i\xi_y p) \tag{53}$$

-continued $$\int_0^\pi d\phi K(k,\xi_y,\phi)\tilde{\eta}\{-R(\theta-\phi)[\hat{x}\sqrt{(2k)^2-\xi_y^2}+\hat{y}\xi_y]\}.$$

By combining the rotations $R(\theta)$ and $R(-\phi)$, we find the integral over $\phi$ is a cyclic convolution. This cyclic convolution can be performed efficiently using the product of Fourier series. To put Eq. (51) into diagonal form, we define the following functions of the data, the kernel, and the structure function:

$$\tilde{S}(k,\xi_p,n_\theta)=\int_{-\infty}^{\infty}\int_{-\pi}^{\pi}dp d\theta \exp(ip\xi_p)\exp(i\theta n_\theta)\tilde{S}(k,p,\theta), \tag{54}$$

$$\tilde{K}(k,\xi_y,n_\theta)=\int_0^\pi d\theta \exp(i\theta n_\theta)K(k,\xi_y,\theta), \tag{55}$$

$$\tilde{\tilde{\eta}}(k,\xi_y,n_\theta)=\int_{-\pi}^{\pi}d\theta \exp(i\theta n_\theta)\tilde{\eta} \tag{56}$$

$$\{-[\hat{x}\cos\theta\sqrt{(2k)^2-\xi_y^2}+\hat{y}\xi_y+\hat{z}\sin\theta\sqrt{(2k)^2-\xi_y^2}]\}.$$

Where $n_\theta$ is an integer on $[-\infty,\infty]$. If we insert the definitions of Eqs. (36)-(38) into Eq. (35), we find the following relationship:

$$\tilde{S}(k,\xi_p,n_\theta)=\tilde{K}(k,\xi_p,n_\theta)\tilde{\tilde{\eta}}(k,\xi_p,n_\theta). \tag{57}$$

In this form we see that $\tilde{S}$ and $\tilde{\tilde{\eta}}$ are related by a diagonal integral operator whose kernel is $\tilde{K}(k',\xi_{p'},n_{\theta'})\delta(k-k')\delta(\xi_p-\xi_{p'})/\delta_{n_\theta,n_{\theta'}}$. Explicitly $S=K\tilde{\eta}$ where $\tilde{K}$ is the integral operator $$\lfloor K\tilde{\eta}\rfloor(k,\xi_p,n_\theta)=\int dk'\int d\xi_{p'} \tag{58}$$

$$\sum_{n_\theta}\tilde{K}(k',\xi_{p'},n_{\theta'})\delta(k-k')\delta(\xi_p-\xi_{p'})\delta_{n_\theta,n_{\theta'}}\tilde{\tilde{\eta}}(k',\xi_{p'},n_{\theta'}).$$

This diagonal operator will simplify finding solutions to specific inverse problems.

The Inverse Problem for Azimuthally-Scanned ISAM

Eq. (57) defines a linear relationship between the object structure and data. To better understand how to invert this relationship, the relationship between the data $\tilde{S}(k,p,\theta)$ and the object $\eta(r)$ is written explicitly:

$$\tilde{S}(k,p,\theta)=\frac{1}{4\pi^2}\int d\xi_y \exp(-i\xi_y p)\sum_{n_\theta=-\infty}^{\infty}\exp(-i\theta n_\theta)K(k,\xi_y,n_\theta) \tag{59}$$

$$\int d^3r \eta(r)\left[\frac{\alpha^2}{k_0}+i(\rho-z_0)\right]^{-1}$$

$$\int_\pi^\pi d\phi \exp(i\phi n_0)\exp\{-ir\cdot R(\phi)[\hat{x}\sqrt{(2k)^2-\xi_y^2}+\hat{y}\xi_y]\}$$

Where $\tilde{K}(k,\xi_p,n_\theta)$ is given explicitly by $$\tilde{K}(k,\xi_p,n_\theta)= \tag{60}$$

-continued $$\frac{i}{2}A(k)\int_0^\pi d\theta \exp(i\theta n_\theta)\exp\left[-\frac{(2k)^2\cos^2\theta + \xi_p^2\sin^2\theta}{2}\frac{\alpha^2}{2k^2}\right]$$

$$\exp\left[-iz_0\sin\theta\sqrt{(2k)^2-\xi_p^2}\right]\sqrt{(2k)^2-\xi_p^2}\sin\theta.$$

Eq. (59) can be rewritten to use a Fredholm-type kernel $\kappa(k, p, \theta, r)$ such that $$S(k,p,\theta)=\kappa\eta=\int d^3r\kappa(k,p,\theta,r)\eta(r). \quad (61)$$

Although Eq. (61) may not be strictly solvable, a least-squares solution $\eta^+$ can be found by minimizing a functional:

$$\eta^+ = \quad (62)$$

$$\operatorname*{argmin}_\eta |S-\kappa\eta|^2 = \operatorname*{argmin}_\eta \int_0^\infty dk \int_{-\infty}^\infty dp \int_{-\pi}^\pi d\theta |S(k,p,\theta)-\kappa\eta(r)|^2.$$

The least-squares solution is then given by the pseudo-inverse $\eta^+=(\kappa^\dagger\kappa)^{-1}\kappa^\dagger S$. While this solution is formally correct, the inverse $(\kappa^\dagger\kappa)^{-1}$ can be difficult to compute in practice. Instead, we find the least-squared error solution for the weighted Fourier transform $\tilde{\eta}^+$ that, while not directly minimizing the error relative to the measurements, still constrains the estimated object structure to be consistent with the data:

$$\tilde{\eta}^+ = \operatorname*{argmin}_{\tilde{\eta}} |S-K\tilde{\eta}|^2 + \lambda|\tilde{\eta}|^2 = \quad (63)$$

$$\operatorname*{argmin}_{\tilde{\eta}} \int_0^\infty dk \int_{-\infty}^\infty d\xi_p$$

$$\sum_{n_\theta=-\infty}^\infty |\tilde{S}(k,\xi_p,n_\theta)-K(k,\xi_p,n_\theta)\tilde{\eta}(k,\xi_p,n_\theta)|^2 +$$

$$\lambda|\tilde{\eta}(k,\xi_p,n_\theta)|^2. \quad$$

This least-squares solution keeps the object estimate consistent with Eq. (57). Also included is a Tikhonov regularization term to stabilize the solution, with regularization parameter $\lambda$. The solution $\tilde{\eta}^+$ is:

$$\tilde{\eta}^+(k,\xi_p,n_\theta) = \frac{\tilde{S}(k,\xi_p,n_\theta)K^*(k,\xi_p,n_\theta)}{|K(k,\xi_p,n_\theta)|^2+\lambda}. \quad (64)$$

This least squares solution is a numerically simpler method of estimating the object structure. Starting with data given by $S(k, p, \theta)$, we can compute $\tilde{S}(k, \xi_p, n_\theta)$ using Eq. (52). Using Eq. (64) one can compute $\tilde{\eta}^+(k,\xi_p, n_\theta)$. Then Eq. (56) can be solved for $\tilde{\eta}^+$ by taking the discrete inverse Fourier transform of $\tilde{\eta}^+$ with respect to $n_\theta$. Finally, a 3-D inverse Fourier transform computes $\eta^+(r)$ from $\tilde{\eta}^+$. In the limit that $\lambda \to 0$ and all data are continuously available, this approach yields an exact solution for $\eta(r)$. In the more realistic scenario that a regularized solution is employed, a stable solution is obtained.

Simulation of Azimuthally-Scanned ISAM

As in the full-field OCT embodiment discussed above, the azimuthally-scanned algorithmic embodiment is now demonstrated by implementing a simulation of the forward and inverse scattering in the radial OCT geometry. A synthetic object was created comprised of pointlike scatterers. The simulated OCT data were calculated from the exact forward problem using Eq. (45), and then the regularized solution of the inverse scattering solution was calculated using Eq. (64). The simulation is of a pseudo-three-dimensional object that is invariant along the y-axis, so that the object is effectively two-dimensional.

The simulation was performed with lengths in units of the central wavelength of the illumination. Typical center wavelengths for OCT imaging are between 800 nm and 1400 nm. The cross-section of the simulated object was taken to be approximately 135 by 135 wavelengths. The Gaussian illumination beam was assumed to be focused 45 wavelengths from the origin, with a beam waist width of 2.5 wavelengths. The scatterers were placed 15 to 60 wavelengths from the origin at randomly selected angles relative to the x-axis. The simulated source was taken to have a Gaussian spectrum with a full-width-half-maximum (FVHM) fractional bandwidth of approximately 25%. Each of the scatterers had the same susceptibility.

Figure 9A:
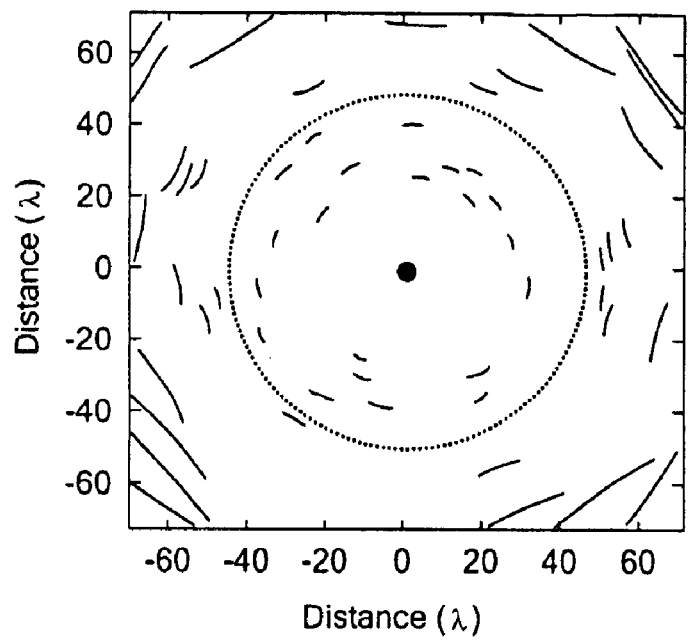
FIG. 9(a) is simulated OCT for randomly scattered point objects and FIG. 9(b) is a reconstruction of the point sources from the simulated data.

The forward scattering problem was implemented by directly summing the contribution of each point scatterer individually using Eq. (45). This was achieved by summing for each sampled data point $\tilde{S}(k,\theta)$ the total collected backscattered amplitude for all of the scatterers at their respective positions r' the amplitude $f^2(r';k)$ as specified in Eq. (44). Note that in Eq. (44) the exact phase rather than the Fresnel quadratic approximation was used to more accurately compute the data for a high numerical aperture beam. To show the equivalent OCT image, the data was inverse Fourier transformed along the k axis, yielding $S(r,\theta)$. The resulting $S(r,\theta)$ is displayed in a polar plot in FIG. 9(a).

The dotted circle in the diagram indicates the radius at which the Gaussian beam is focused. Note that the images of points located closer to the origin than the focus (inside the circle) curve towards the origin, and the points located further from the origin than the focus curve (outside the circle) away from the origin, as would be expected.

The inverse scattering problem was implemented using the approximate solution embodied in Eq. (64). The data is given as $\tilde{S}(k,\theta)$. To utilize Eq. (64), several Fourier transform steps were needed. The inverse scattering algorithm was implemented using the following steps:

The data $\tilde{S}(k,\theta)$ was Fourier transformed with respect to $\theta$ to yield $\tilde{S}(k,n_\theta)$.

The function $\tilde{K}(k,\theta)$ was calculated (using $\xi_p=0$) and then Fourier transformed with respect to $\theta$ to yield $k(k, n_\theta)$ as per Eq. (61).

The regularized $\tilde{\eta}^+(k,n_\theta)$ was calculated using Eq. 65.

$\tilde{\eta}^+(k,n_\theta)$ was inverse Fourier transformed with respect to $n_\theta$ to yield $\tilde{\eta}^+(k,\theta)$.

The $\tilde{\eta}^+(k,\theta)$ was inverse Fourier transformed with respect to k to yield $\eta_R^+(l,\theta)$, the Radon transform of $\eta^+(x,z)$.

The inverse Radon transform of $\eta_R^+(l,\theta)$ was performed to yield $\eta^+(x,z)$, the Tikhonov-regularized inverse.

The inverse Radon transform was used as a convenient way to convert from the polar representation of the Fourier transform $\tilde{\eta}^+(k,\theta)$ to its inverse Fourier transform Cartesian counterpart $\eta^+(x,z)$, using the Fourier projection slice theorem. Unfortunately, many implementations of the inverse Radon transform, such as the filtered-backprojection method that was used for this simulation, are slow, and therefore care will need to be exercised to ensure that the computational burden is not too great. Methods exist to implement the inverse Radon transform in $O(N^2 \log N)$ time, rather than the $O(N^3)$ typical of most filtered-backprojection inverse Radon transform methods.

Figure 9B:
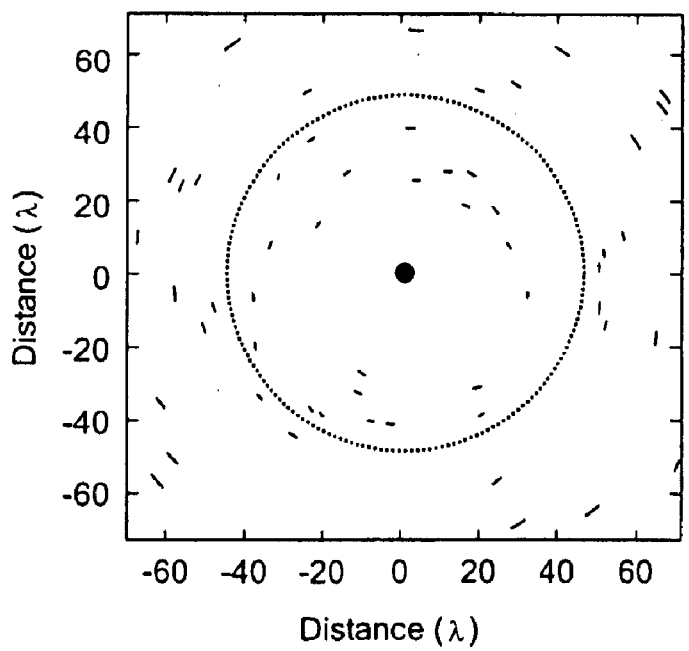

The results of the inverse scattering computation are shown in FIG. 9(b). As can be seen, the blurred arcs corresponding to the point sources in the uncorrected OCT data are corrected to be pointlike when inverse scattering is performed on the data. The algorithm correctly compensates for the range-dependent blur and curvature of the backscattered signal. Unlike in the translationally-scanned Gaussian beam or the full-field cases, the reconstructed image does not exhibit uniform resolution. The resolution of the reconstruction depends on the distance from the origin. Because the beam width is wide near the origin, points nearer the origin than the focus are overlapped by the beam for many angles θ, so that the resolution of points near the origin is high. At the focus, the beam width is narrow and so points near the focus are also resolved well. Far from the origin, the beam is wide and points are only overlapped by the beam for a narrow range of angles given by the divergence of the beam, so that the resolution degrades with distance from the origin. Generally, the resolution is nearly constant between the origin and the focus radius, and slowly degrades to a constant angular resolution at radii further than the focus. Therefore, the most useful resolution will be achieved for distances at or closer than the focus radius.

Figure 10:
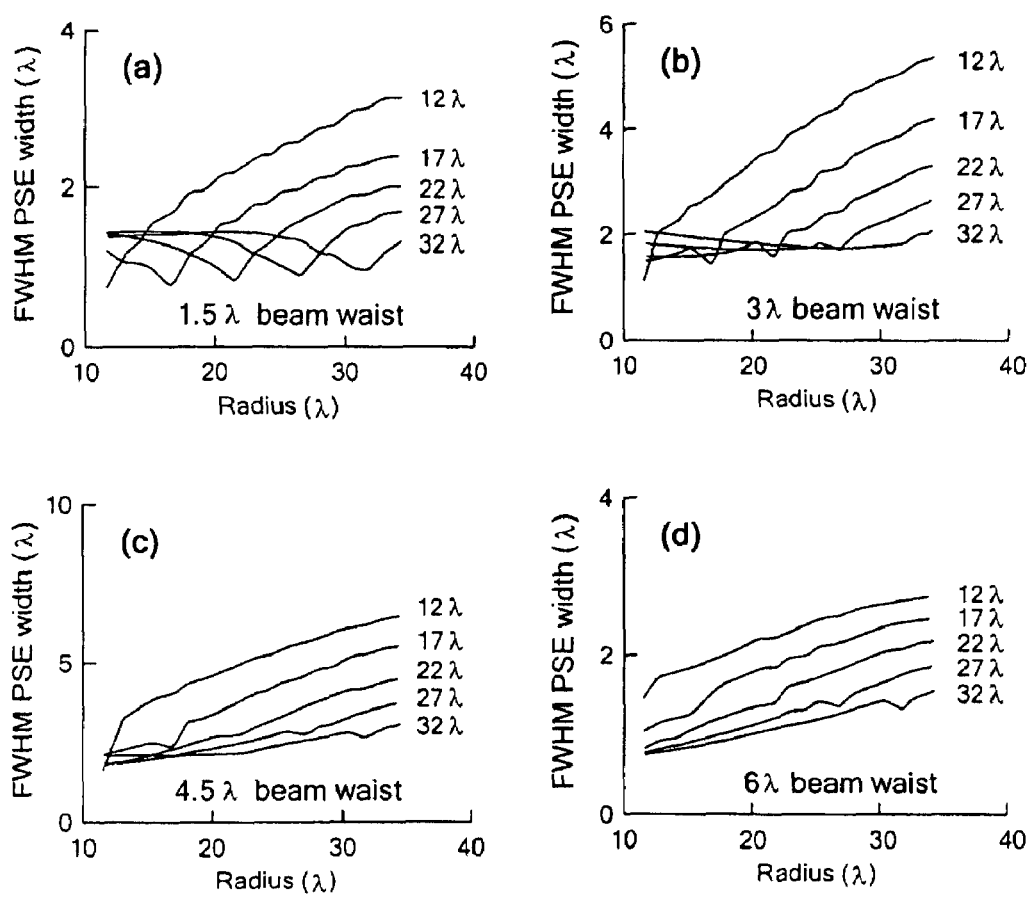
FIG. 10 is a plot depicting full-width-half-maximum transverse point-spread-function (PSF) resolution of simulated point sources situated at different distances from the catheter axis, as a function of focus radius and beam width. The abscissa is the distance from the origin from which the simulated point source is placed. In each part, the number next to each curve is the distance away from the origin the beam was focused. The beam waist for each part is (a) 1.5λ, (b) 3λ, (c) 4.5λ, and (d) 6λ.

To explore the range-dependent resolution further, a simulation of point scatterers reconstructed with beams with various widths and focus radii is now described with reference to FIG. 10. FIG. 10 has four parts, each of which is the simulated resolution of point scatterers for beams of different widths. The marking next to each curve is the focus radius for each simulated beam. The resolution is measured as the FWHM of the reconstructed point in the angular direction. Each graph relates the FWHM resolution to the distance from the axis to the simulated point. For small beam waists, as in parts (a), (b), and (c), the resolution is approximately constant for radii closer than the focus radius. Further than the focus the FVHM resolution starts to increase. For the wider beams, the transverse resolution near the origin can be somewhat better than the width of the beam waist.

Figure 11:
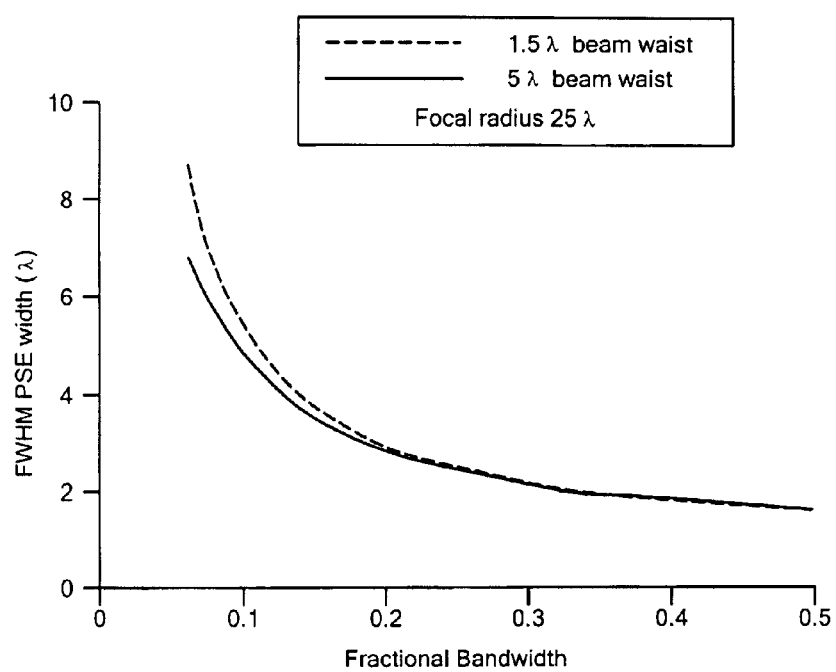
FIG. 11 is a plot depicting full-width-half-maximum axial resolution of simulated point sources imaged with two different beam widths focused 25 wavelengths from the catheter axis, for various fractional bandwidths of the source. The dotted curve corresponds to a 1.5λ beam waist, while the solid curve corresponds to a 5λ beam waist.

To examine the validity of the approximation made in Eq. 47 of small fractional bandwidth, we simulate the reconstruction of point scatterers imaged with various source bandwidths. The simulated focus radius is 25 wavelengths, and the beam widths are 1.5 and 5 wavelengths. FIG. 11 shows the FVHM axial resolution as a function of fractional bandwidth. The resolution should be approximately half the reciprocal of the fractional bandwidth, to which the simulation conforms.

Phase Stability in ISAM

The increased resolution gained by the ISAM solution relies upon phase stable measurements. The phases in cross-correlation signals correspond to the measured relative delay between the reference and sample signal at particular temporal frequencies of the illumination. The aforementioned methods rely on the phases of the cross-correlation measurements for a particular data set to correspond, i.e. the relative delays measured for various positions of the illumination beam need to reflect the true delays for the beam to scatter off of layers inside the object. Unfortunately, because of motions and changes in the object during the data acquisition, and thermal fluctuations that cause object dimensions to change, these delays can vary during the data acquisition interval. This is a problem for almost all computed imaging modalities, but can be exacerbated for optical imaging because the small size of the illumination wavelength (often less than a micron) means that very small motions can cause relatively large fluctuations in phase. If the data acquisition is brief, and the reference delay mechanism can produce a reliably repeatable delay to an accuracy of less than a wavelength, then phase stability between measurements can be easily achieved. For example, with the use of spectral detection for OCT, spectral-domain OCT (SD-OCT) seen in FIG. 6, we can be assured of phase stability within each axial data set because the reference mirror is typically fixed and the data acquisition is very rapid, typically occurring in fractions of a second. Specifically, each axial acquisition is determined directly from Fourier transform of the ensemble of spectral intensity measurements over the duration of the exposure time on a CCD camera. Thus, relative phases between adjacent reflections in the sample are fixed relative to each other and the reference for a single axial acquisition. Furthermore, if adjacent axial scans may be captured fast enough to avoid some minimum amount of phase drift then an accurate reconstruction is possible. Phase drift can occur in a system for multiple reasons including thermal changes, galvanometer or stage positioning accuracy, and system or sample jitter. The greater the time interval between scans, the more likely it is that random phase errors will occur. Adjacent axial scans in a single cross-sectional scan are thus less likely to suffer from distortions due to random phase jitter than adjacent axial scans from multiple cross-sectional scans.

Object reconstruction requires the phase to be stable relative to all axial scans of a 3D acquisition. There are several ways to achieve phase stability, whether it is one of many hardware and environmental configurations, implementations of reference objects, or algorithmic developments based on priors. In conventional scanned beam OCT, it has been shown by Ralston et al., *Phase Stability Technique for Inverse Scattering in Optical Coherence Tomography*, IEEE International Symposium on Biomedical Imaging., pp. 578-581, (2006), incorporated herein by reference, that one such possible method to achieve 3D phase stability in OCT for reconstruction of the inverse scattering solution is to use a flat reference reflector such as a microscope coverslip. Because the coverslip typically remains in contact with the object, its position relative to the object is fixed, and therefore can serve to indicate a delay that is consistent between axial scans. Such a method offers advantages over expensive environmental controllers and extremely fast acquisition hardware. Further, we develop an algorithm for tracking the air-glass interface. Other interfaces that are fixed relative to the object being measured can also be used, such as the interior or exterior surface of the transparent wall of a catheter.

The acquired SD-OCT signal can be represented after dispersion correction as a function of transverse position and wave number, $S(r_o,k)$, where the wave numbers k are related to the frequencies ω by the dispersion relation $k(\omega)=\omega n/c$, and n is the index of refraction.

We present a method that analyzes each axial scan individually and applies a phase to compensate variations of the position of the sample relative to the illumination beam. We place a reflective surface such as a microscope coverslip on top of the sample to act as a reference surface, which is used to infer the delay to the top surface of the sample. The signal for an arbitrary axial line of data can be represented as S(k), a function of k. We assume that there is a range of distances along the illumination beam $z_{min}$ to $z_{max}$ for which the signal reflected from the coverslip is known to reside in every axial scan. The inverse Fourier transform of S(k) is computed as $S_c(z)$, and the signal corresponding to the reflection is contained in the samples $S_c(z)$ for $z_{min} \leq z \leq z_{max}$. The spatial spectrum of the reflection is computed as the Fourier transform of $S_c(z)$ over the window $z_{min} \leq z \leq z_{max}$, which is called $\tilde{S}_c(k)$.

Because the signal contained in $\tilde{S}_c(k)$ corresponds to a single reflection, it is reasonable to model it as $\tilde{S}_c(k) = A(k)e^{e\phi(k)}$, where the phase function $\phi(k) = \phi_0 + kd$, where $\phi_0$ is an arbitrary phase and d is the true position of the surface where the reference reflection occurs. Because of the motion of the sample, the actual phase arg $\tilde{S}_c(k) = \phi'(k)$. By multiplying the axial scan data S(k) by the correction factor $e^{i[\phi(k)-\phi'(k)]}$, the phase of the axial scan can be adjusted to place the reflection at its true known position d.

We model the phase $\phi'(k)$, as a Taylor series around a center frequency $k_0$:

$$\phi'(k) = \phi'(k_0) + (k - k_0)\frac{\partial \phi'}{\partial k}\bigg|_{k=k_0} + \dots,$$

To utilize this model, we must estimate the value of $\partial\phi'/\partial k|_{k=k_0}$ from the data function $\phi'(k)$. The function $\phi'(k)$ is wrapped to the range $-\pi$ to $\pi$, so calculating the derivative directly from the wrapped data will incorrectly incorporate the $2\pi$ jumps into the estimate. Instead, we form the unwrapped $\phi_w(k)$ by removing $2\pi$ discontinuities from $\phi'(k)$. The estimate then becomes $$\frac{\partial \phi'}{\partial k}\bigg|_{k=k_0} \approx \frac{\phi_w(k_2) - \phi_w(k_1)}{k_2 - k_1}$$

where $k_1 < k_0 < k_2$, with the frequencies $k_1$ and $k_2$ chosen to span the illumination spectrum, typically with $k_1$ and $k_2$ corresponding to the frequencies at which the power spectral density is half of that at the peak.

Once $\phi'(k_0)$ and $\partial\phi'/\partial k|_{k=k_0}$ are known, the empirical $\phi'(k)$ can be computed, and the corrected axial scan spectrum $S'(k) = S(k)e^{i[\phi(k)-\phi(k')]}$. This corrected axial scan data will be modified such that the position of the reference reflection is always at the same location on the axial scan, removing the effective longitudinal relative motion between the sample and the scanned beam. For this method to work properly, the reference object must be located for each axial scan, otherwise that axial scan could contribute to a poor reconstruction. Furthermore, refinements to this method could utilize higher order terms of the series for $\phi'(k)$, which would account for instrument dispersion as well as motion.

Experimental Examples of ISAM Imaging

Figure 12:
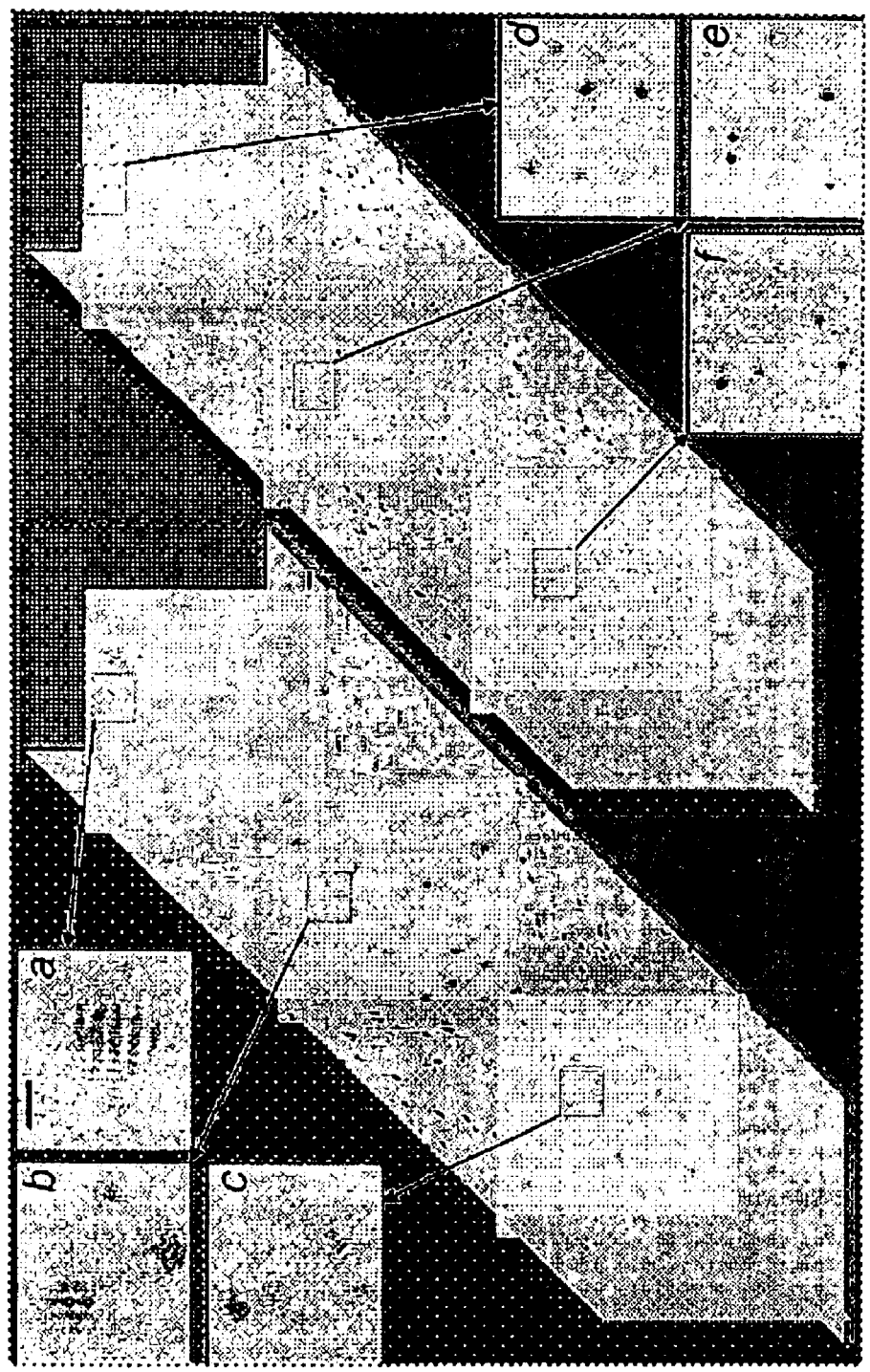
FIG. 12 shows interferometric data from a tissue phantom consisting of titanium dioxide scatterers suspended in silicone. Planar slices the 3-D unprocessed data (left) and ISAM reconstruction (right) are shown for two en face planes above the focus and one below the focus. Magnified unprocessed sections for three depths are shown in (a) at z=1100 µm, (b) at z=475 µm, and (c) at z=−240 µm, where z=0 µm is the focal plane. Magnified ISAM reconstructions for these corresponding planes are shown in (d), (e), and (f), respectively. The scale bar represents 18 µm.

A tissue phantom consisting of a collection of titanium dioxide scatterers having a mean diameter of 1 μm and uniformly suspended in silicone was imaged using low-coherence interferometry and a 0.05 NA objective. FIG. 12 displays cross-sections through an unprocessed data set (left) and ISAM reconstruction (right) of a volume 360 μm×360 μm (transverse)×2000 μm (axial). FIG. 12 a-f contain three pairs of en face sections for both the unprocessed data (FIG. 12 a-c) and the ISAM reconstructions (FIG. 12 d-j). The distances from the en face section planes to the focus, located at z=0, are z=1100 μm (FIGS. 12a and 12a), z=475 μm (FIGS. 12b and 12e), and z=−240 μm (FIGS. 12c and 12f). These sections show that the reconstruction has resolved the scatterers throughout a range of depths over nine times the Rayleigh range from the focus, where the Rayleigh range is commonly defined as half of the depth-of-field, or what is considered in-focus in optical imaging systems. In the unprocessed data, the interference between the signals scattered from adjacent scatterers is evident. Our method properly accounts for the diffraction of the beam, and so separates the superimposed signals from the scatterers to form well-resolved point images on all planes.

Figure 13:
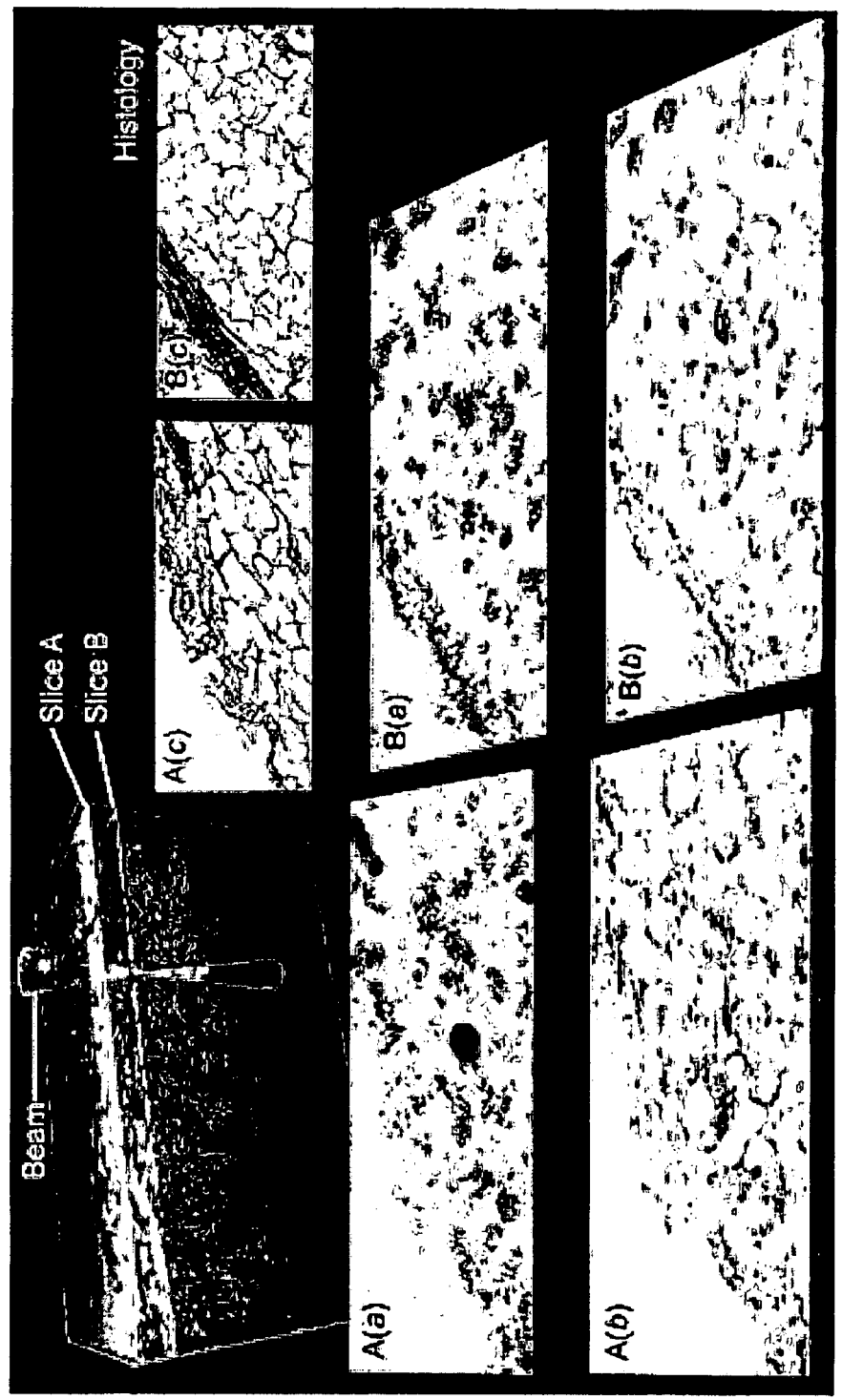
FIGS. 13(a)-(c) show en face images from human breast tissue. (a) Unprocessed interferometric data and (b) ISAM reconstructions are shown for depths located at z=591 µm (Slice A) and z=643 µm (Slice B), where z=0 µm is the focal plane. (c) The corresponding histological sections are shown for comparison.

Human tumor tissue was resected and imaged ex vivo. Sections were marked with India ink after imaging and before embedding to register locations. FIG. 13 includes en face planes (Slices A and B) of the unprocessed data (FIG. 13a) where the beam diffraction effects are evident, the computed ISAM reconstructions (FIG. 13b), and images of corresponding registered histological sections (FIG. 13c). Although embedding, sectioning, and staining of tissue can disrupt features to some degree, the registered histological sections provide prominent features for comparison. In the reconstruction, boundaries between adipose cells and the margin between adipose and fibrous tissue are clearly identified, with a strong correspondence to histology. While the histological images were obtained by destroying the sample, ISAM could readily be applied for in vivo applications because signal collection is in the back-scattered epi-direction.

Real-Time Cross-Sectional Processing

In order to provide the benefits of spatially-invariant resolution attainable by means of the hitherto described features of ISAM and to obtain immediate feedback in time-critical situations or for monitoring transient dynamics, methods are now described for real-time realization of ISAM computations.

As described in detail above, an object being imaged by spectral-domain OCT (SD-OCT) has a susceptibility represented by $\eta(r_\parallel, z)$, where $r_\parallel$ is the transverse position and z is the longitudinal position. The collected SD-OCT signal is represented by $\tilde{S}(r_\parallel, \omega)$, whose arguments are the transverse position of the beam $r_\parallel$ and the frequency $\omega$. After correcting for dispersion, the signal is represented by $\tilde{S}(r_\parallel, k)$, where k is the uniformly spaced wavenumber. The Fourier transform of $\tilde{S}(r_\parallel, k)$ with respect to k is $S(r_\parallel, t)$. Introducing a coordinate change from t to t' such that t'=0 coincides with the delay of the focal plane results in a signal $S(r_\parallel, t')$. The 3-D Fourier transform of $S(r_\parallel, t')$ is $\tilde{S}(Q, k)$.

The algorithm for ISAM is constructed as described above. A solution for high-numerical aperture optics is implemented, namely, a relation is derived that associates the Fourier transform of the object η with the Fourier transform of the signal S. The 2-D Fourier transform of the spectral-domain OCT signal $\tilde{S}(r_\parallel, k)$, is given by the expression $$\tilde{S}(Q, k) = \frac{k^2}{\alpha^2} i2\pi^2 A(k) \frac{e^{-2ik_z(Q/2)z_0}}{k_z(Q/2)} e^{-\frac{u^2 Q^2}{2k^2}} \tilde{\eta}[Q, 2k_z(Q/2)], \quad (65)$$

where $\tilde{\eta}$ is the 3-D Fourier transform of η, the argument Q is the transverse wavevector, k is the wavenumber, $k_z(q) = \sqrt{k^2 - q^2}$, $z_0$ is the fixed position of the beam focus, A(k) is the square root of the power spectral density, $\alpha = \pi/NA$, and NA is the numerical aperture of the beam. The corresponding Tikhonov regularized solution, $\tilde{\eta}^+$, takes the form $$\tilde{\eta}^+(Q,\beta) = \left[\frac{f^*(Q,k,\beta)\tilde{S}(Q,k)}{|f(Q,k,\beta)|^2 + 2\lambda k/k_z(Q/2)}\right]_{k=\frac{1}{2}\sqrt{\beta^2-Q^2}} \quad (66)$$

where $$f(Q,k,\beta) = \frac{k^2}{\alpha^2} i2\pi^2 A(k) \frac{e^{-2ik_z(Q/2)z_0}}{k_z(Q/2)} e^{\frac{\alpha^2 Q^2}{4k^2}}, \quad (67)$$

$\beta$ is the longitudinal frequency coordinates of the object, and $\lambda$ is the regularization constant. Rearranging the terms of the Fourier space into multiplicative factors of magnitude, $\tilde{B}(Q,k)$, and phase, $e^{i(2k_z(Q/2)z_0+\pi/2)}$, the pseudo inverse can be rewritten as $$\tilde{\eta}^+(Q,\beta) = \tilde{B}(Q,k) e^{i(2k_z(Q/2)z_0+\pi/2)} \tilde{S}(Q,k)\Big|_{k=\frac{1}{2}\sqrt{\beta^2+Q^2}}, \quad (68)$$

where $$\tilde{B}(Q,k) = \frac{-\frac{k}{\alpha^2}\pi^2 A(k) e^{\frac{\alpha^2 Q^2}{4k^2}}}{\frac{k^3}{\alpha^4}\frac{2\pi^4 A^2(k)}{k_z(Q/2)} e^{\frac{-\alpha^2 Q^2}{2k^2}} + \lambda}. \quad (69)$$

Without loss of generality, the same origin is designated for the depth coordinates z as the time delay coordinates t. The t=0 delay corresponds to the z=0 plane and coincide at the path length matched delay of the reference. Additionally, for a coordinate change, the t'=0 delay corresponds to the z'=0 plane and coincide at the focal plane, where then $z_0$ will equal zero, and equation (66) reduces to $$\tilde{\eta}^{+'}(Q,\beta) = \tilde{B}(Q,k) e^{i\pi/2} \tilde{S}(Q,k)\Big|_{k=\frac{1}{2}\sqrt{\beta^2+Q^2}}. \quad (70)$$

Figure 15:
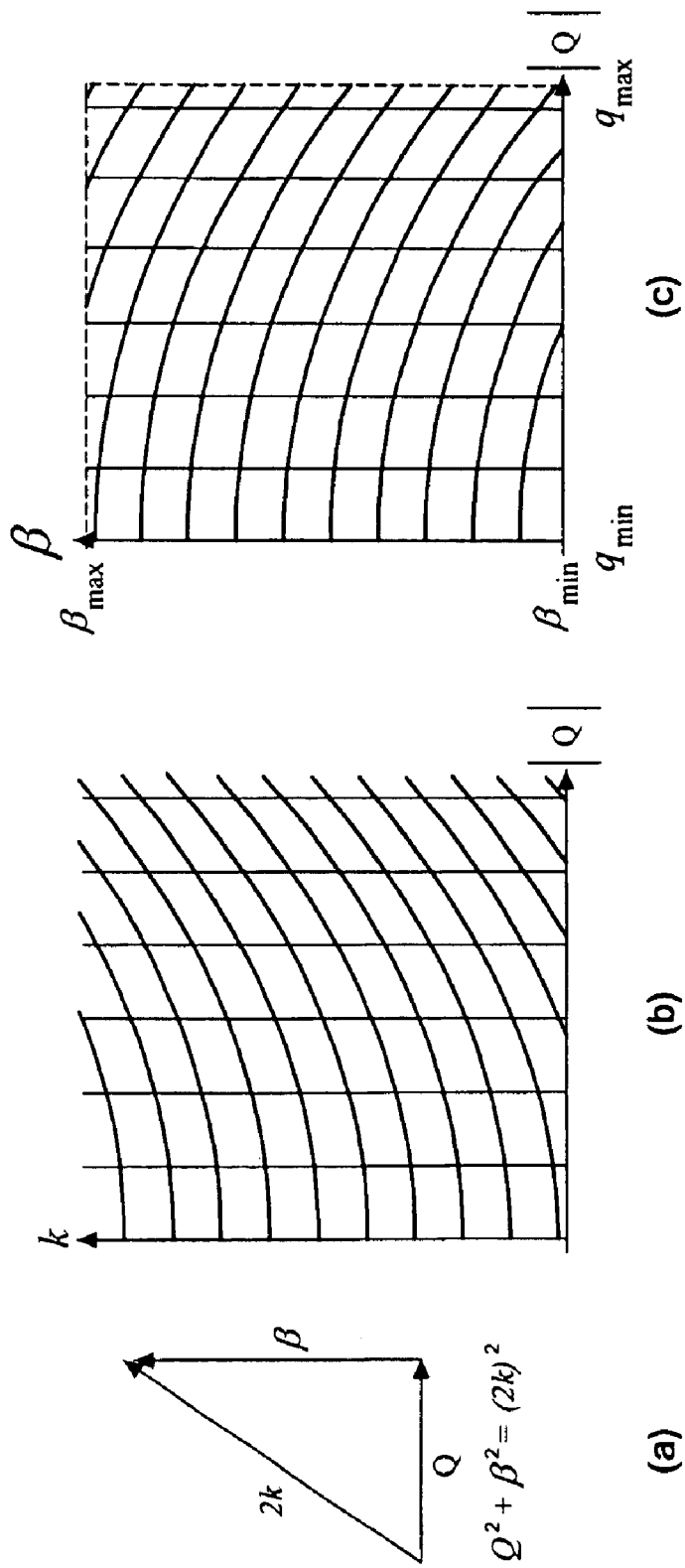
FIG. 15(a) depicts the relation between spatial frequencies of the signal space and spatial frequencies in the object space.
FIG. 15(b) shows a sampling lattice for selected (β, |Q|) values on a uniform (k, |Q|) grid.
FIG. 15(c) shows a sampling lattice for selected (k, |Q|) values on a uniform (β, |Q|) grid.

A coordinate change from t to t' is achieved by circularly shifting the data. The origin of the t coordinates is at the time corresponding to the arrival of the reference light. The origin of the t' coordinates is shifted such that t'=0 is at the focal plane. A zero pad of $2|t_0|$ rows prevents aliasing of the shifted data, where $t_0$ is the number of delay samples from the focus to t'=0. The model in FIG. 15(a) and the grid in FIGS. 15(b) and (c) describe visually in 2D the ISAM resampling seen in equation (70).

A shift of $t_0$ in $S(r_\parallel,t)$ is used to make the t=0 delay coincide with the z=0 plane as will be seen in the algorithm. $S(r_\parallel,t+t_0)$ has the Fourier transform relation $\tilde{S}(Q,k)e^{-kQt_0}$. If we substitute this into the equation.

$$\tilde{\eta}(Q,\beta) = \tilde{B}(Q,k) e^{2ik_z(Q/2)z_0} \tilde{S}(Q,k) e^{-kQt_0}\Big|_{k=\frac{1}{2}\sqrt{\beta^2+Q^2}} \quad (71)$$

$$\tilde{\eta}^+(Q,\beta) = \tilde{B}(Q,k) i e^{i(2k_z(Q/2)z_0-kt_0)} \tilde{S}(Q,k)\Big|_{k=\frac{1}{2}\sqrt{\beta^2+Q^2}} \quad (72)$$

This equation may be simplified by having the relative time offset $t_0$ and the focus offset $z_0$ coincide at $t_0=0$ and $z_0=0$.

Figure 16:
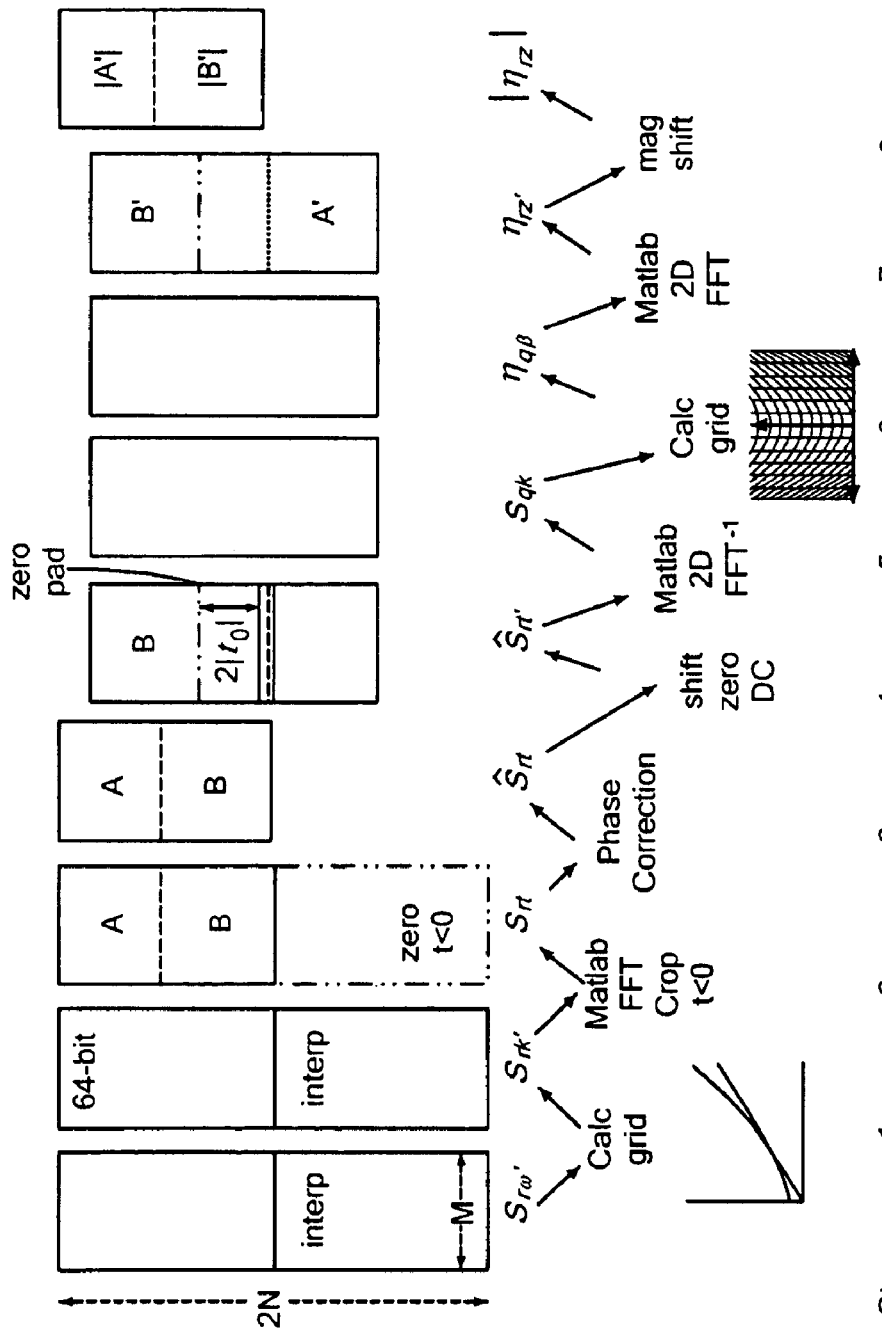
FIG. 16 is a data flow chart for ISAM processing, in accordance with embodiments of the present invention.

FIG. 16 shows a data flow diagram for the prototype ISAM algorithm for 2D imaging where in the paraxial limit $r_\parallel$ now describes a single transverse dimension. It is noted that the other transverse dimension may be solved separately in so much as the paraxial approximation holds. The prototype algorithm was designed in Matlab, a mathematical software package, where all the calculations were done in double precision, 64-bit. The digitized spectra $S_{r\omega}$ is a function of the M discrete positions r in the plane perpendicular to the beam axis and the N discrete frequencies $\omega$. A non-uniform interpolation is needed to map the sampled frequencies $\omega$ to the sampled wavenumbers k. Similarly, the ISAM solution requires a non-uniform interpolation mapping wavenumbers k to longitudinal frequency coordinates of the object $\beta$. The cubic B-spline is chosen as the non-uniform resampling interpolator; although, a windowed sinc interpolator, such as the prolate-spheroidal interpolator, may be chosen to select specific convergence characteristics. Unfortunately, the frequency response for many non-uniform interpolation procedures drops in performance for frequencies higher than half the Nyquist rate. To mitigate this effect, each spectrum is interpolated by performing a fast Fourier transform (FFT), padding with N zeros, and performing an inverse FFT (IFFT). The interpolated spectra are stored in a buffer with 2N rows and M columns. Thus, the new interpolated, digitized spectra $S_{r\omega'}$ is a function of the sampled positions r and the new sampled frequencies $\omega'$. Similarly, $S_{rk}$ is interpolated by a factor of 2 to get $S_{rk'}$ as a function of r and the new uniformly sampled wavenumbers k'.

The non-uniformly sampled spectrum in spectral-domain OCT can be corrected in a fashion similar to material dispersion correction by resampling the Fourier spectrum from $\omega'$ to k. A desired reindexing array $i_n$ is based primarily on calibrated, second- and third-order correction factors $\alpha_2$ and $\alpha_3$, respectively.

$$i_n = 2n + \alpha_2\left(\frac{2n}{N} - \omega_{ctr}\right)^2 + \alpha_3\left(\frac{2n}{N} - \omega_{ctr}\right)^3, \quad (73)$$

where n is an integer between 0 and N−1, 2N is the number of samples of the interpolated spectrum $S_{r\omega'}$, and $\omega_{ctr}$ is the calculated centroid of the spectrum on a scale from 0 to 1. $\alpha_2$ and $\alpha_3$ are set through a calibration routine. A mirror models a perfect reflector with a minimized width of the point spread function (PSF). Thus, $\alpha_2$ and $\alpha_3$ are adjusted such that the imaged PSF is indeed minimized.

FIG. 16 shows a data flow chart of the prototype algorithm which has been broken down into the eight steps listed below.

Step 1 The spline coefficients and interpolations are computed as described above. The result is stored in an array $S_{rk'}$ where k' is the uniformly sampled wavenumber.

Step 2 The 1-D FFT of the columns of $S_{rk'}$ is taken to get the signal $S_{rt}$ where t is the sampled time delay of the optical signal. The Hermitian symmetric values, where t<0, are removed. There will be no ambiguity, if the reference arm is placed such that the reference light pulse arrives at the spectrometer before the sample light pulses. The complex analytic OCT signal is represented by $S_{rt}$.

Step 3 A phase correction procedure is implemented to ensure phase stability for the ISAM reconstruction. A glass coverslip can be placed on top of the sample to track and reduce system instabilities. The phase corrected signal is represented as $\hat{S}_{rt}$.

Step 4 The contribution of the constant spectral intensity is removed by setting $\hat{S}_{rt}$ to zero, for values near t=0. Then, a coordinate change from t to t' is made by circularly shifting the rows such that the focal plane lies at t'=0, which coincides with z'=0 where the solution is derived in equation (72). The data $\hat{S}_{rt'}$ is padded with $2|t_0|$ rows of zeros to prevent aliasing of the shifted data, where $t_0$ is the number of time delay samples from the focus to the center of $\hat{S}_{rt'}$.

Step 5 The 2-D IFFT of $\hat{S}_{rt'}$ is taken to get $S_{qk}$.

Step 6 The 2-D ISAM resampling grid, spline coefficients, and the interpolations are calculated. Then the result is multiplied by $\tilde{B}(Q,k)e^{i\pi/2}$ to get $\eta_{q\beta}$.

Step 7 The 2-D FFT of $\eta_{q\beta}$ is taken to get $\eta_{rz'}$, where z'=0 at the focal plane.

Step 8 A coordinate change from z' to z is made by circularly shifting the rows such that the reference delay lies at the top of the image and corresponds to the z=0 plane. Then, the magnitude of the ISAM reconstruction $\eta_{rz}$ is calculated resulting in ISAM amplitude image $|\eta_{rz}|$.

There are a number of operations hindering the performance of the prototype ISAM algorithm. Using C++ instead of Matlab allows for a number of speed improvements. The 64-bit operations such as the FFT and interpolations can be replaced with 32-bit operations with a small, but tolerable, increase of quantization noise. A speed advantage is gained by replacing the 'for' loops within Matlab scripts by vectorized Intel SSE (Streaming SIMD Extentions) commands and/or compiled 'for' loops. Time-expensive, built-in Matlab interpolation and FFT functions are replaced with hardware optimized functions as found in the Intel Math Kernel Library (MKL). An FFT of the real spectrum is implemented using the customized real-to-complex FFT in the MKL. The resampling step corrects the depth dependent defocus and is crucial for the performance of the algorithm. Although, the filter in equation (72), $\tilde{B}(Q,k)e^{i\pi/2}$, can be highly singular which introduces noise, hence the need for regularization. Furthermore, applying the filter provides a quantitative, but not a significant qualitative change to the data. Thus, equation (72) is reduced to an unfiltered solution $$\tilde{\eta}^{+''}(Q,\beta) = \tilde{S}(Q,k)\Big|_{k=\frac{1}{2}\sqrt{\beta^2+Q^2}} \quad (74)$$

without degradation of the Fourier space resampling. The focal plane is fixed such that $t_0=0$ by imposing a restriction that the focus be placed at the center of the image. Therefore, the complex analytic signal does not need to be padded with any zeros, and thus the computation time of the FFT is reduced because the FFT is always a power of two. While the prototype functions utilized dynamically allocated memory, the real-time program allocates memory prior to imaging time. Similarly, a table of resampling coefficients for the dispersion compensation and the ISAM reconstruction are pre-calculated and stored in memory. The prototype algorithm interpolated the data by two to mitigate the high frequency roll-off of the non-uniform interpolator. Although the interpolation has good frequency response, it is not necessary, especially when speed is an issue. The phase stabilization procedures, which might be needed for long acquisition periods, are not necessary for 2-D imaging since this SD-OCT system provides good phase stability over the short duration of the scan, about 17 ms.

The key computation for ISAM is the resampling in the Fourier space. The new design is an efficient routine which requires two interpolations of the columns, one one-dimensional (1D) real-to-complex (R2C) fast Fourier transform (FFT) of the columns, and two 2D FFTs. The FFT routine from the Intel Math Kernel Library (MKL) was used for all 1D and 2D transforms. The ID 2048-point R2C FFT is calculated for every column of the 512×2048 real-valued data, while the 2D FFT and 2D IFFT are calculated for the 512×1024 complex values.

The reindexing array $i_n$ and the corresponding cubic B-spline interpolation table is pre-computed and stored in random access memory (RAM) for repeated use. The coefficients for the cubic B-spline are pre-computed. The integer part of the index used for calculation of the in the cubic B-spline is given by $$a_x[n] = \begin{cases} \lfloor i_n \rfloor + x, & 0 \le \lfloor i_n \rfloor + x \le N-1 \\ 0, & \lfloor i_n \rfloor + x < 0 \\ N-1, & \lfloor i_n \rfloor + x > N-1 \end{cases}, x=-1,0,1,2 \text{ and } 0 \le n < N \quad (75)$$

The fractional coefficients are given by $$f_n = i_n - \lfloor i_n \rfloor, 0 \le n < N \quad (76)$$

and $$b_{-1}[n] = (1-f_n)^3/6$$
$$b_0[n] = (4-6f_n^2+3f_n^3)/6,$$
$$b_1[n] = (1+3f_n+3f_n^2-3f_n^3)/6, 0 \le n < N \quad (77)$$
$$b_2[n] = f_n^3/6$$

Next, the Fourier resampling indices of ISAM are pre-calculated. The constants which specify the axial and transverse bandwidths of the object, based on system parameters, are $\beta_{min}$, $\beta_{max}$, $q_{min}$, and $q_{max}$, respectively. These constants are selected in accordance to the specific bandwidth parameters of the system and describe the boundaries of the Fourier space shown in FIG. 15(c). By defining the longitudinal bandwidth parameters of the object rather than the wavenumber, we can avoid computationally costly zeropadding of the resampled solution. However, a small loss of spectral information across the $\beta_{min}$ boundary may reduce the signal-to-noise ratio, but only marginally. In this case, $\beta_{min}$ and $\beta_{max}$ are set to be the boundaries of the optical bandwidth, $q_{min}$ is set to zero, and $q_{max}$ is set to the maximum transverse scanning frequency. More important than the exact values for $\beta_{min}$, $\beta_{max}$, $q_{min}$, and $q_{max}$, is the ratio of the corresponding transverse and longitudinal bandwidths. The maximum and minimum wavenumber are calculated for the region of interest, $$k_{min} = \beta_{min}/2, \quad (78)$$

$$k_{max} = 0.5\sqrt{\beta_{max}^2+q_{max}^2}. \quad (79)$$

A range of values for q[m] and β[n] is created in the 2-D Fourier space and the resampling grid kq[m,n] is pre-calculated. Notice here that M and N'=N/2 are assigned according to number of rows and columns in the complex analytic sampled Fourier data.

$$q[m] = \begin{cases} m\dfrac{2q_{max}}{M}, & 0 < m \le M/2 \\ (m-M)\dfrac{2q_{max}}{M}, & M/2 < m \le M \end{cases}, \quad (80)$$

-continued $$\beta[n] = n(\beta_{\max} - \beta_{\min})/N' + \beta_{\min}, \ 0 \le n < N', \quad (81)$$

$$kq[m, n] = \frac{N'}{k_{\max} - k_{\min}} \left(0.5\sqrt{\beta[n]^2 + q[m]^2} - k_{\min}\right) + 1, \quad (82)$$

$$0 < n < N', \ 0 < m < M$$

The kq[m,n] grid is used to calculate a table of values for the cubic B-spline coefficients. The values are calculated as shown above except each column of resampling parameters is different and therefore must also be saved. FIG. 1(b) shows the plot of the kq[m,n] grid where the curved lines represent the constant values of β[n]. This 2D grid is used to calculate another table of cubic B-spline coefficients. The spline values are calculated as shown above except each column of the resampling parameters is different and therefore 2D spline coefficients are stored in memory.

Similar to the spline coefficient calculations shown above, the reindexing array kq[m,n] and the corresponding cubic B-spline interpolation coefficient table is pre-computed and stored in random access memory (RAM) for repeated use. The integer part of the index used for calculation of the in the cubic B-spline is given by $$a'_{q,x}[m, n] = \begin{cases} \lfloor kq[m, n] \rfloor + x, & 0 \le \lfloor kq[m, n] \rfloor + x \le N' - 1 \\ 0, & \lfloor kq[m, n] \rfloor + x < 0 \\ N' - 1, & \lfloor kq[m, n] \rfloor + x > N' - 1 \end{cases} ; \quad (83)$$

$$x = -1, 0, 1, 2;$$

$$0 \le n < N'; 0 \le m < M$$

The fractional coefficients are given by $$f_{m,n} = kq[m,n] - \lfloor kq[m,n] \rfloor, \ 0 \le n < N'; \ 0 \le m < M \quad (84)$$

and $$b'_{q,-1}[m,n] = (1-f_{m,n})^3/6$$

$$b'_{q,0}[m,n] = (4 - 6f_{m,n}^2 + 3f_{m,n}^3)/6$$

$$b'_{q,1}[m,n] = (1 + 3f_{m,n} + 3f_{m,n}^2 - 3f_{m,n}^3)/6, \ 0 \le n < N'; \quad (85)$$
$$0 \le m < M$$

$$b'_{q,2}[m,n] = f_{m,n}^3/6$$

Figure 17:
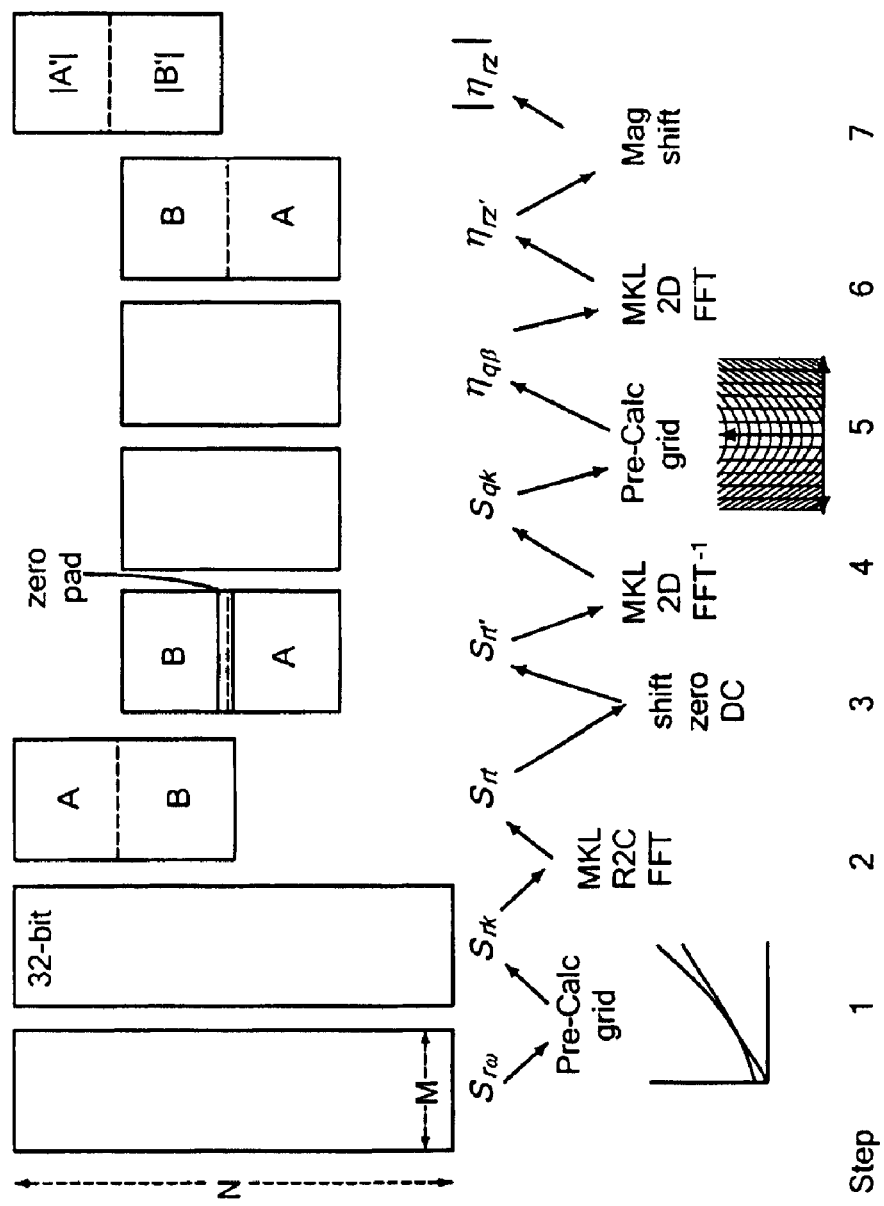
FIG. 17 is a computational flow chart for memory allocation for successive steps of ISAM processing, in accordance with embodiments of the present invention.

Using the pre-calculated tables, a flow diagram of the real-time algorithm is shown in FIG. 17.

Here $S_{r\omega}[m,n]$ is the raw interferometric data captured from the camera and has M columns and N rows. In this implementation, M=512 columns and N=2048 rows.

Step 1 The pre-calculated table is used to perform the interpolation as follows.

$$S_{rk}[m,n] = S_{r\omega}[m, a_{-1}\{n\}]b_{-1}\{n\} + S_{r\omega}[m, a_0\{n\}]b_0\{n\} + S_{r\omega}[m, a_1\{n\}]b_1\{n\} + S_{r\omega}[m, a_2\{n\}]b_2\{n\} \quad (86)$$

for all integers $0 \le n < N$ and $0 \le m < M$.

Step 2 The real-to-complex 1-D FFT routine from the Intel Math Kernel Library (MKL) is used on all the columns.

$$S_{rt}[m, n] = \sum_{k=0}^{N-1} S_{rk}[m, k] e^{-\frac{2\pi i}{N} k n}, \ 0 \le nN \text{ and } 0 \le m < M \quad (87)$$

The real-to-complex FFT will compute N/2 complex values. The new number of rows of the complex data is given by N'=N/2.

Step 3 The contribution of the noise from the average spectral intensity on the detector is removed by setting $S_{rt}[m,n]$ equal to zero at the t=0 plane. Also, $S_{rt}[m,n]$ is circularly shifted by half such that the focus will be the new t'=0 plane.

$$S_{rt'}[m, n] = \quad (88)$$

$$\begin{cases} S_{rt}[m, n + N'/2] & 0 \le n < N'/2 \\ 0 & N'/2 \le n < N'/2 + 2 \text{ and } 0 \le m < M. \\ S_{rt}[m, n - N'/2] & N'/2 + 2 \le n < N' \end{cases}$$

Step 4 The complex 2-D inverse FFT (IFFT) of the complex analytic signal $S_{rt'}[m,n]$ is calculated $$S_{qk}[m, n] = \frac{1}{MN'} \sum_{r=0}^{M-1} \sum_{t=0}^{N'-1} S_{rt'}[r, t] e^{\frac{2\pi i}{N'} nt} e^{\frac{2\pi i}{M} mr}, \quad (89)$$

$$0 \le n < N' \text{ and } 0 \le m < M.$$

Step 5 The pre-calculated table is used to perform the cubic B-spline interpolation as follows.

$$\eta_{q\beta}[m,n] = S_{qk}[m, a'_{q,-1}\{m,n\}]b'_{q,-1}\{m,n\} + S_{qk}[m, a'_{q,0}\{m,n\}]b'_{q,0}\{m,n\} + S_{qk}[m, a'_{q,1}\{m,n\}]b'_{q,1}\{m,n\} + S_{qk}[m, a'_{q,2}\{m,n\}]b'_{q,2}\{m,n\}, 0 \le n < N' \text{ and } 0 \le m < M, \quad (90)$$

where the calculated cubic B-spline coefficients are from the lookup table.

Step 6 The complex 2-D FFT of the Fourier transformed object $\eta_{q\beta}[m,n]$ is calculated $$\eta_{rz'}[m, n] = \sum_{q=0}^{M-1} \sum_{\beta=0}^{N'-1} \eta_{q\beta}[q, \beta] e^{-\frac{2\pi i}{N'} \beta n} e^{-\frac{2\pi i}{M} qm}, \quad (91)$$

$$0 \le n < N' \text{ and } 0 \le m < M.$$

Step $\eta_{rz'}[m,n]$ is circularly shifted such that the focus is in the middle of the image, $$\eta_{rz}[m, n] = \begin{cases} \eta_{rz'}[m, n + N'/2] & 0 \le n < N'/2 \\ \eta_{rz'}[m, n - N'/2] & N'/2 \le n < N' \end{cases}, \quad (92)$$

then the magnitude $|\eta_{rz}[m,n]|$ is displayed.

In various embodiments of the present invention, the disclosed methods determining the three-dimensional susceptibility of a sample may be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g. the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The embodiments of the invention heretofore described are intended to be merely exemplary and numerous variations and modifications will be apparent to those skilled in the art. All such variations and modifications are intended to be within the scope of the present invention as defined in any appended claims.

What is claimed is:

1. A method for determining the three-dimensional susceptibility of a sample, the method comprising:
    a. providing a source of a beam of radiation characterized by a temporally dependent spectrum and a local propagation axis defined at a locus of incidence with respect to a surface of the sample;
    b. irradiating the surface in a plane characterized by a fixed displacement along the propagation axis of the beam;
    c. superposing scattered radiation from the sample with a reference beam derived from the source of the beam of radiation to provide an interference signal;
    d. deriving a forward scattering model relating measured data to structure of an object; and
    e. solving an inverse scattering problem based upon the forward scattering model and the interference signal to infer a three-dimensional structure of the sample.

2. A method in accordance with claim 1, wherein the step of providing a source of a beam of radiation includes providing a partially coherent source.

3. A method in accordance with claim 1, wherein the step of deriving a forward scattering model further includes relating a transform of measured data to a transform of structure of the sample.

4. A method in accordance with claim 3, further comprising a step of transforming the interference sign into a transform of the interference signaling a transform domain.

5. A method in accordance with claim 1, wherein the step of solving an inverse scattering problem is performed in substantially real time.

6. A method in accordance with claim 1, wherein the step of irradiating includes focusing radiation substantially at the surface of the sample.

7. A method in accordance with claim 6, wherein the step of focusing includes illuminating the sample through a microscope objective.

8. A method in accordance with claim 1, wherein the step of irradiating the sample includes delivering the beam to the sample by at least one of a catheter, a needle, a probe, and endoscope, and a laparoscope.

9. A method in accordance with claim 1, further comprising sweeping the spectrum of the source of radiation as a function of time.

10. A method in accordance with claim 1, wherein the step of providing a source includes providing a tunable laser.

11. A method in accordance with claim 1, wherein the step of superposing includes configuring arms of the beam of radiation in an interferometer.

12. A method in accordance with claim 11, wherein the step of superposing includes configuring arms of the beam in one of a Michelson, a Mach-Zehnder, and a Fizeau interferometer.

13. A method in accordance with claim 1, wherein the step of superposing the scattered radiation and reference beam includes superposition with a modulated reference beam and phase-sensitive detection of the interference signal.

14. A method in accordance with claim 1, further comprising interposing a reference reflector along the local propagation axis.

15. A method in accordance with claim 1, wherein the step of interposing a reference reflector includes interposing a microscope coverslip.

16. A computer program product for use on a computer system for determining the three-dimensional susceptibility of a sample, the computer program product comprising a computer usable medium having computer readable program code thereon, the computer readable program code including:
    a. an input for receiving an interference signal obtained through superposition of scattered light from the sample with a reference beam;
    b. program code for deriving a forward scattering model relating measured data to structure of an object; and
    c. program code for solving an inverse scattering problem based upon the forward scattering model and the interference signal to infer a three-dimensional structure of the sample.

* * * * *